United States Patent
Arendze-Bailey et al.

(10) Patent No.: US 9,790,513 B2
(45) Date of Patent: Oct. 17, 2017

(54) STRESS INDUCIBLE DERIVATIVE PROMOTER

(71) Applicant: UNIVERSITY OF CAPE TOWN, Cape Town (ZA)

(72) Inventors: Bronwyn Lynn Arendze-Bailey, Diep River (ZA); Jennifer Ann Thomson, Constantia (ZA); Kershini Iyer, Century (ZA); Mohamed Suhail Rafudeen, Rylands (ZA); Revel Iyer, Century (ZA); Tamaryn Lorean Ellick, Steenberg (ZA)

(73) Assignee: UNIVERSITY OF CAPE TOWN, Cape Town (ZA)

( * ) Notice: Subject to any disclaimer, the term of this patent is extended or adjusted under 35 U.S.C. 154(b) by 288 days.

(21) Appl. No.: 14/426,445

(22) PCT Filed: Sep. 9, 2013

(86) PCT No.: PCT/IB2013/058399
§ 371 (c)(1),
(2) Date: Mar. 6, 2015

(87) PCT Pub. No.: WO2014/037919
PCT Pub. Date: Mar. 13, 2014

(65) Prior Publication Data
US 2015/0307891 A1 Oct. 29, 2015

(30) Foreign Application Priority Data

Sep. 10, 2012 (ZA) .................................. 2012/06750

(51) Int. Cl.
C12N 15/82 (2006.01)
C07K 14/415 (2006.01)

(52) U.S. Cl.
CPC ........ *C12N 15/8237* (2013.01); *C07K 14/415* (2013.01)

(58) Field of Classification Search
None
See application file for complete search history.

(56) References Cited

U.S. PATENT DOCUMENTS

2005/0155114 A1 7/2005 Hinchey

FOREIGN PATENT DOCUMENTS

WO 2009060402 A2 5/2009

OTHER PUBLICATIONS

Odour. Functional Analysis of the Novel Stress- Inducible XVPSAP promoter isolated from Xerophya Viscosa. University of Cape Town. 2009. pp. 1-178.*
International Search Report from corresponding to PCT/IB2013/058399, mailed Jan. 27, 2014.

(Continued)

*Primary Examiner* — Ashley K Buran
(74) *Attorney, Agent, or Firm* — McBee Moore Woodward & Vanik IP, LLC

(57) ABSTRACT

The present invention relates to abiotic stress-inducible derivative promoters from *Xerophyta viscosa*, nucleotide cassettes, recombinant vectors, cells and transgenic plants containing the promoter in operable linkage with a heterologous transcribable DNA sequence.

17 Claims, 15 Drawing Sheets

(56) References Cited

OTHER PUBLICATIONS

Ellerstrom et al. "Functional dissection of a napin gene promoter: identification of promoter elements required for embryo and endosperm-specific transcription", Plant Molecular Biology 32:, pp. 1019-1027, 1996, XP001007602.

Dolferus et al., "Differential Interactions of Promoter Elements in Stress Responses of the Arabidopsis Adh Gene", Plant Physiol., vol. 105, 1994, 105: pp. 1075-1087, XP002031338.

Oduor, "Functional Analyses of the Novel Stress-Inducible XVPSAP Promoter Isolated from Xerophyta Viscosa", University of Cape Town, Feb. 2009, XP007922468.

Iyer et al. "XvSapl, a Desiccation Tolerance Associated Gene with Potential for Crop Improvement", XP008104609, pp. 283-296.

Saka et al., "Analysis of the Promoter of the Auxin-Inducible Gene, parC, of Tobacco", Plant Cell Physiol. 37(7): pp. 906-913, Tokyo, Japan, 1996, XP055095471.

Wang et al., "Two single-base substitutions involved in altering in a paired-box of AAATAC in the promoter region of soybean lipoxygenase L-3 gene impair the promoter function in tobacco cells", ELSEVIER, Plant Science 109, 1995, pp. 67-73, XP055095480.

\* cited by examiner

```
1      ACTGTCTGGG TAGCTGGCAA TATAGAGACG TAAATAATTG TCTGTAAATA GGGAGAAATT
61     CATGGATCAT CACCCTAATT CGGTCTTTCA CTCATTTTAT CATAGACCTG ACTAAAGAAC
121    TTGGTCAGAG TTTTTACTTA TTTAAAATAA AGAGGACTTC ATGGCATCCA TGTGCAGGTA
181    CAGCTCCCAG AAAAAAAAGC ATGAAACACG AGAGGATCAA TAGCATTCGA TCTGAAACAA
241    AAGGTTGCAG CTCAAGACTT TCTCCAAAAT ATTAAGATGA TCCAAAGAAT TACCCCAAGA
301    TATCCAACGT ATACCAATGT GTATACCGAA AGTAAGAAAG TTCACGTGCA TTCTTTGATT
361    TTTCTCCCGA GTGTTCTTTT CTGAAATGAG TAAATAAGAC TAGAATAAGA GCTAATGTAT
421    TTTTTTTCTA AAAAAAGTTG AATGTGGATA CAATATGATT ATACATTCAT TAGCTATTTT
481    AAGTATATTC TATTTTTTTT CCCCCCAAAA GAACACAAAT GTGTTCCGTC ACTTTCCATG
541    GAGATCAGAT CTATCTTAGA ATTGGACAGG GTGCTTATGA TACAACTTGT TCCTATCAAC
601    AACTGCATGT TAGACAGCGC CGAATTTACA GTCCTACTGG GCGCCACTTT TCAACCCACA
661    TCATCAAGAT GAACACCACG TTATCTTCAT CCGCTCCAAC CACATGGTCC AGCGCCACTG
721    GCCAAGACCG CCAGCCAGCC AGGCCATCCA ACGTGGTGCA TTTTCTAACA CTCCACGTTC
781    GCTGTACGGC ATTATTTCTC CAGCCAGAAA GACCGAGACA GCGACGCTGT TGGGCGGGCC
841    CGCGGCCTGC TCTCTCTGCT TCCCCATGAG ATTCACGGGC ATCGCTCCTC GCTCGTGCCT
901    ACGCGACCGC GCCGATCCAC GTGACGTGGC GCAGCAATCG TTCTTACTAG GCGCTTGCAC
961    GTGTCGTTCG CATGCGAAGC GTCCACACTG CCAACGACCT CCTTAAATAT CCTTGTGATA
1021   TTCGCCTTAC GATCTCACAC TTCGCACGCA AAGGCCAGTC GCAGATTTGG GTTGAATTTG
1081   CTGCGTTTTG GCAGATTTTG AGCGAGAGAT ATTAGGGAAG
```

Figure 1

```
1      ACTGTCTGGG TAGCTGGCAA TATAGAGACG TAAATAATTG TCTGTAAATA GGGAGAAATT
61     CATGGATCAT CACCCTAATT CGGTCTTTCA CTCATTTTAT CATAGACCTG ACTAAAGAAC
121    TTGGTCAGAG TTTTTACTTA TTTAAAATAA AGAGGACTTC ATGGCATCCA TGTGCAGGTA
181    CAGCTCCCAG AAAAAAAAGC ATGAAACACG AGAGGATCAA TAGCATTCGA TCTGAAACAA
241    AAGGTTGCAG CTCAAGACTT TCTCCAAAAT ATTAAGATGA TCCAAAGAAT TACCCCAAGA
301    TATCCAACGT ATACCAATGT GTATACCGAA AGTAAGAAAG TTCACGTGCA TTAGATCTCA
361    GATCTATCTT AGAATTGGAC AGGGTGCTTA TGATACAACT TGTTCCTATC AACAACTGCA
421    TGTTAGACAG CGCCGAATTT ACAGTCCTAC TGGGCGCCAC TTTTCAACCC ACATCATCAA
481    GATGAACACC ACGTTATCTT CATCCGCTCC AACCACATGG TCCAGCGCCA CTGGCCAAGA
541    CCGCCAGCCA GCCAGGCCAT CCAACGTGGT GCATTTTCTA ACACTCCACG TTCGCTGTAC
601    GGCATTATTT CTCCAGCCAG AAAGACCGAG ACAGCGACGC TGTTGGGCGG GCCCGCGGCC
661    TGCTCTCTCT GCTTCCCCAT GAGATTCACG GCATCGCTC CTCGCTCGTG CCTACGCGAC
721    CGCGCCGATC CACGTGACGT GGCGCAGCAA TCGTTCTTAC TAGGCGCTTG CACGTGTCGT
781    TCGCATGCGA AGCGTCCACA CTGCCAACGA CCTCCTTAAA TATCCTTGTG ATATTCGCCT
841    TACGATCTCA CACTTCGCAC GCAAAGGCCA GTCGCAGATT TGGGTTGAAT TTGCTGCGTT
901    TTGGCAGATT TTGAGCGAGA GATATTAGGG AAG
```

Figure 2

```
1      ACTGTCTGGG TAGCTGGCAA TATAGAGACG TAAATAATTG TCTGTAAATA GGGAGAAATT
61     CATGGATCAT CACCCTAATT CGGTCTTTCA CTCATTTTAT CATAGACCTG ACTAAAGAAC
121    TTGGTCAGAG TTTTTACTTA TTTAAAATAA AGAGGACTTC ATGGCATCCA TGTGCAGGTA
181    CAGCTCCCAG AAAAAAAAGC ATGAAACACG AGAGGATCAA TAGCATTCGA TCTGAAACAA
241    AAGGTTGCAG CTCAAGACTT TCTCCAAAAT ATTAAGATGA TCCAAAGAAT TACCCCAAGA
301    TATCCAACGT ATACCAATGT GTATACCGAA AGTAAGAAAG TTCACGTGCA TTAGACAGAT
361    CTACGTGGTG CATTTTCTAA CACTCCACGT TCGCTGTACG GCATTATTTC TCCAGCCAGA
421    AAGACCGAGA CAGCGACGCT GTTGGGCGGG CCCGCGGCCT GCTCTCTCTG CTTCCCCATG
481    AGATTCACGG GCATCGCTCC TCGCTCGTGC CTACGCGACC GCGCCGATCC ACGTGACGTG
541    GCGCAGCAAT CGTTCTTACT AGGCGCTTGC ACGTGTCGTT CGCATGCGAA GCGTCCACAC
601    TGCCAACGAC CTCCTTAAAT ATCCTTGTGA TATTCGCCTT ACGATCTCAC ACTTCGCACG
661    CAAAGGCCAG TCGCAGATTT GGGTTGAATT TGCTGCGTTT TGGCAGATTT TGAGCGAGAG
721    ATATTAGGGA AG
```

Figure 3

```
1      CTTCCCTAAT ATCTCTCGCT CAAAATCTGC CAAAACGCAG CAAATTCAAC CCAAATCTGC
61     GACTGGCCTT TGCGTGCGAA GTGTGAGATC GTAAGGCGAA TATCACAAGG ATATTTAAGG
121    AGGTCGTTGG CAGTGTGGAC GCTTCGCATG CGAACGACAC GTGCAAGCGC CTAGTAAGAA
181    CGATTGCTGC GCCACGTCAC GTGGATCGGC GCGGTCGCGT AGGCACGAGC GAGGAGCGAT
241    GCCCGTGAAT CTCATGGGGA AGCAGAGAGA GCAGGCCGCG GGCCCGCCCA ACAGCGTCGC
301    TGTCTCGGTC TTTCTGGCTG GAGAAATAAT GCCGTACAGC GAACGTGGAG TGTTAGAAAA
361    TGCACCACGT TGGATGGCCT GGCTGGCTGG CGGTCTTGGC CAGTGGCGCT GGACCATGTG
421    GTTGGAGCGG ATGAAGATAA CGTGGTGTTC ATCTTGATGA TGTGGGTTGA AAAGTGGCGC
481    CCAGTAGGAC TGTAAATTCG GCGCTGTCTA ACATGCAGTT GTTGATAGGA CAAGTTGTA
541    TCATAAGCAC CCTGTCCAAT TCTAAGATAG ATCTGATCTC CATGGAAAGT GACGGAACAC
601    ATTTGTGTTC TTTTGGGGGG AAAAAAAATA GAATATACTT AAAATAGCTA ATGAATGTAT
661    AATCATATTG TATCCACATT CAACTTTTTT TAGAAAAAAA ATACATTAGC TCTTATTCTA
721    GTCTTATTTA CTCATTTCAG AAAAGAACAC TCGGGAGAAA AATCAAAGAA TGCACGTGAA
781    CTTTCTTACT TTCGGTATAC ACATTGGTAT ACGTTGGATA TCTTGGGGTA ATTCTTTGGA
841    TCATCTTAAT ATTTTGGAGA AAGTCTTGAG CTGCAACCTT TTGTTTCAGA TCGAATGCTA
901    TTGATCCTCT CGTGTTTCAT GCTTTTTTTT CTGGGAGCTG TACCTGCACA TGGATGCCAT
961    GAAGTCCTCT TTATTTTAAA TAAGTAAAAA CTCTGACCAA GTTCTTTAGT CAGGTCTATG
1021   ATAAAATGAG TGAAAGACCG AATTAGGGTG ATGATCCATG AATTTCTCCC TATTTACAGA
1081   CAATTATTTA CGTCTCTATA TTGCCAGCTA CCCAGACAGT
```

Figure 4

```
1    CTTCCCTAAT ATCTCTCGCT CAAAATCTGC CAAAACGCAG CAAATTCAAC CCAAATCTGC
61   GACTGGCCTT TGCGTGCGAA GTGTGAGATC GTAAGGCGAA TATCACAAGG ATATTTAAGG
121  AGGTCGTTGG CAGTGTGGAC GCTTCGCATG CGAACGACAC GTGCAAGCGC CTAGTAAGAA
181  CGATTGCTGC GCCACGTCAC GTGGATCGGC GCGGTCGCGT AGGCACGAGC GAGGAGCGAT
241  GCCCGTGAAT CTCATGGGGA AGCAGAGAGA GCAGGCCGCG GGCCCGCCCA ACAGCGTCGC
301  TGTCTCGGTC TTTCTGGCTG GAGAAATAAT GCCGTACAGC GAACGTGGAG TGTTAGAAAA
361  TGCACCACGT TGGATGGCCT GGCTGGCTGG CGGTCTTGGC CAGTGGCGCT GGACCATGTG
421  GTTGGAGCGG ATGAAGATAA CGTGGTGTTC ATCTTGATGA TGTGGGTTGA AAAGTGGCGC
481  CCAGTAGGAC TGTAAATTCG GCGCTGTCTA ACATGCAGTT GTTGATAGGA CAAGTTGTA
541  TCATAAGCAC CCTGTCCAAT TCTAAGATAG ATCTGAGATC TAATGCACGT GAACTTTCTT
601  ACTTTCGGTA TACACATTGG TATACGTTGG ATATCTTGGG GTAATTCTTT GGATCATCTT
661  AATATTTTGG AGAAAGTCTT GAGCTGCAAC CTTTTGTTTC AGATCGAATG CTATTGATCC
721  TCTCGTGTTT CATGCTTTTT TTTCTGGGAG CTGTACCTGC ACATGGATGC CATGAAGTCC
781  TCTTTATTTT AAATAAGTAA AAACTCTGAC CAAGTTCTTT AGTCAGGTCT ATGATAAAAT
841  GAGTGAAAGA CCGAATTAGG GTGATGATCC ATGAATTTCT CCCTATTTAC AGACAATTAT
901  TTACGTCTCT ATATTGCCAG CTACCCAGAC AGT
```

Figure 5

```
1    CTTCCCTAAT ATCTCTCGCT CAAAATCTGC CAAAACGCAG CAAATTCAAC CCAAATCTGC
61   GACTGGCCTT TGCGTGCGAA GTGTGAGATC GTAAGGCGAA TATCACAAGG ATATTTAAGG
121  AGGTCGTTGG CAGTGTGGAC GCTTCGCATG CGAACGACAC GTGCAAGCGC CTAGTAAGAA
181  CGATTGCTGC GCCACGTCAC GTGGATCGGC GCGGTCGCGT AGGCACGAGC GAGGAGCGAT
241  GCCCGTGAAT CTCATGGGGA AGCAGAGAGA GCAGGCCGCG GGCCCGCCCA ACAGCGTCGC
301  TGTCTCGGTC TTTCTGGCTG GAGAAATAAT GCCGTACAGC GAACGTGGAG TGTTAGAAAA
361  TGCACCACGT AGATCTGTCT AATGCACGTG AACTTTCTTA CTTTCGGTAT ACACATTGGT
421  ATACGTTGGA TATCTTGGGG TAATTCTTTG GATCATCTTA ATATTTTGGA GAAAGTCTTG
481  AGCTGCAACC TTTTGTTTCA GATCGAATGC TATTGATCCT CTCGTGTTTC ATGCTTTTTT
541  TTCTGGGAGC TGTACCTGCA CATGGATGCC ATGAAGTCCT CTTTATTTTA AATAAGTAAA
601  AACTCTGACC AAGTTCTTTA GTCAGGTCTA TGATAAAATG AGTGAAAGAC CGAATTAGGG
661  TGATGATCCA TGAATTTCTC CCTATTTACA GACAATTATT TACGTCTCTA TATTGCCAGC
721  TACCCAGACA GT
```

Figure 6

```
1    ATGGTCACCG ACGCCAAAAA CATAAAGAAA GGCCCGGCGC CATTCTATCC GCTGGAAGAT
61   GGAACCGCTG GAGAGCAACT GCATAAGGCT ATGAAGAGAT ACGCCCTGGT TCCTGGAACA
121  ATTGCTTTTA CAGATGCACA TATCGAGGTG GACATCACTT ACGCTGAGTA CTTCGAAATG
181  TCCGTTCGGT TGGCAGAAGC TATGAAACGA TATGGGCTGA ATACAAATCA CAGAATCGTC
241  GTATGCAGTG AAAACTCTCT TCAATTCTTT ATGCCGGTGT TGGGCGCGTT ATTTATCGGA
301  GTTGCAGTTG CGCCCGCGAA CGACATTTAT AATGAACGTG AATTGCTCAA CAGTATGGGC
361  ATTTCGCAGC CTACCGTGGT GTTCGTTTCC AAAAAGGGGT TGCAAAAAAT TTTGAACGTG
421  CAAAAAAAGC TCCCAATCAT CCAAAAAATT ATTATCATGG ATTCTAAAAC GGATTACCAG
481  GGATTTCAGT CGATGTACAC GTTCGTCACA TCTCATCTAC CTCCCGGTTT TAATGAATAC
541  GATTTTGTGC CAGAGTCCTT CGATAGGGAC AAGACAATTG CACTGATCAT GAACTCCTCT
601  GGATCTACTG GTCTGCCTAA AGGTGTCGCT CTGCCTCATA GAACTGCCTG CGTGAGATTC
661  TCGCATGCCA GAGATCCTAT TTTTGGCAAT CAAATCATTC CGGATACTGC GATTTAAGT
721  GTTGTTCCAT TCCATCACGG TTTTGGAATG TTTACTACAC TCGGATATTT GATATGTGGA
781  TTTCGAGTCG TCTTAATGTA TAGATTTGAA GAAGAGCTGT TTCTGAGGAG CCTTCAGGAT
841  TACAAGATTC AAAGTGCGCT GCTGGTGCCA ACCCTATTCT CCTTCTTCGC CAAAAGCACT
901  CTGATTGACA AATACGATTT ATCTAATTTA CACGAAATTG CTTCTGGTGG CGCTCCCCTC
961  TCTAAGGAAG TCGGGGAAGC GGTTGCCAAG AGGTTCCATC TGCCAGGTAT CAGGCAAGGA
1021 TATGGGCTCA CTGAGACTAC ATCAGCTATT CTGATTACAC CCGAGGGGGA TGATAAACCG
1081 GGCGCGGTCG GTAAAGTTGT TCCATTTTTT GAAGCAAGG TTGTGGATCT GGATACCGGG
1141 AAAACGCTGG GCGTTAATCA AGAGGCGAA CTGTGTGTGA GAGGTCCTAT GATTATGTCC
1201 GGTTATGTAA ACAATCCGGA AGCGACCAAC GCCTTGATTG ACAAGGATGG ATGGCTACAT
1261 TCTGGAGACA TAGCTTACTG GGACGAAGAC GAACACTTCT TCATCGTTGA CCGCCTGAAG
1321 TCTCTGATTA AGTACAAAGG CTATCAGGTG GCTCCCGCTG AATTGGAATC CATCTTGCTC
1381 CAACACCCCA ACATCTTCGA CGCAGGTGTC GCAGGTCTTC CCGACGATGA CGCCGGTGAA
1441 CTTCCCGCCG CCGTTGTTGT TTTGGAGCAC GGAAAGACGA TGACGGAAAA AGAGATCGTG
1501 GATTACGTCG CCAGTCAAGT AACAACCGCG AAAAAGTTGC GCGGAGGAGT TGTGTTTGTG
1561 GACGAAGTAC CGAAAGGTCT TACCGGAAAA CTCGACGCAA GAAAAATCAG AGAGATCCTC
1621 ATAAAGGCCA AGAAGGGCGG AAAGATCGCC GTGTAA
```

Figure 7

```
1   GAGTACGGTG GGTAGCCCGA TCGTTCAAAC ATTTGGCAAT AAAGTTTCTT AAGATTGAAT
61  CCTGTTGCCG GTCTTGCGAT GATTATCATA TAATTTCTGT TGAATTACGT TAAGCATGTA
121 ATAATTAACA TGTAATGCAT GACGTTATTT ATGAGATGGG TTTTTATGAT TAGAGTCCCG
181 CAATTATACA TTTAATACGC GATAGAAAAC AAAATATAGC GCGCAAACTA GGATAAATTA
241 TCGCGCGCGG TGTCATCTAT GTTACTAGAT CCCTAGGCTA TCTGTCACTT CATCAAAAGG
```

Figure 8

```
1     AGTACTTTAA AGTACTTTAA AGTACTTTAA AGTACTTTGA TCCAACCCCT CCGCTGCTAT
61    AGTGCAGTCG GCTTCTGACG TTCAGTGCAG CCGTCTTCTG AAAACGACAT GTCGCACAAG
121   TCCTAAGTTA CGCGACAGGC TGCCGCCCTG CCCTTTTCCT GGCGTTTTCT TGTCGCGTGT
181   TTTAGTCGCA TAAAGTAGAA TACTTGCGAC TAGAACCGGA GACATTACGC CATGAACAAG
241   AGCGCCGCCG CTGGCCTGCT GGGCTATGCC CGCGTCAGCA CCGACGACCA GGACTTGACC
301   AACCAACGGG CCGAACTGCA CGCGGCCGGC TGCACCAAGC TGTTTTCCGA GAAGATCACC
361   GGCACCAGGC GCGACCGCCC GGAGCTGGCC AGGATGCTTG ACCACCTACG CCCTGGCGAC
421   GTTGTGACAG TGACCAGGCT AGACCGCCTG GCCCGCAGCA CCCGCGACCT ACTGGACATT
481   GCCGAGCGCA TCCAGGAGGC CGGCGCGGGC CTGCGTAGCC TGGCAGAGCC GTGGGCCGAC
541   ACCACCACGC CGGCCGGCCG CATGGTGTTG ACCGTGTTCG CCGGCATTGC CGAGTTCGAG
601   CGTTCCCTAA TCATCGACCG CACCCGGAGC GGGCGCGAGG CCGCCAAGGC CCGAGGCGTG
661   AAGTTTGGCC CCGCCCTAC CCTCACCCCG GCACAGATCG CGCACGCCCG CGAGCTGATC
721   GACCAGGAAG GCCGCACCGT GAAAGAGGCG GCTGCACTGC TTGGCGTGCA TCGCTCGACC
781   CTGTACCGCG CACTTGAGCG CAGCGAGGAA GTGACGCCCA CCGAGGCCAG GCGGCGCGGT
841   GCCTTCCGTG AGGACGCATT GACCGAGGCC GACGCCCTGG CGGCCGCCGA GAATGAACGC
901   CAAGAGGAAC AAGCATGAAA CCGCACCAGG ACGGCCAGGA CGAACCGTTT TCATTACCG
961   AAGAGATCGA GGCGGAGATG ATCGCGGCCG GGTACGTGTT CGAGCCGCCC GCGCACGTCT
1021  CAACCGTGCG GCTGCATGAA ATCCTGGCCG GTTTGTCTGA TGCCAAGCTG GCGGCCTGGC
1081  CGGCCAGCTT GGCCGCTGAA GAAACCGAGC GCCGCCGTCT AAAAAGGTGA TGTGTATTTG
1141  AGTAAAACAG CTTGCGTCAT GCGGTCGCTG CGTATATGAT GCGATGAGTA AATAAACAAA
1201  TACGCAAGGG GAACGCATGA AGGTTATCGC TGTACTTAAC CAGAAAGGCG GGTCAGGCAA
1261  GACGACCATC GCAACCCATC TAGCCCGCGC CCTGCAACTC GCCGGGGCCG ATGTTCTGTT
1321  AGTCGATTCC GATCCCCAGG GCAGTGCCCG CGATTGGGCG GCCGTGCGGG AAGATCAACC
1381  GCTAACCGTT GTCGGCATCG ACCGCCCGAC GATTGACCGC GACGTGAAGG CCATCGGCCG
1441  GCGCGACTTC GTAGTGATCG ACGGAGCGCC CCAGGCGGCG GACTTGGCTG TGTCCGCGAT
1501  CAAGGCAGCC GACTTCGTGC TGATTCCGGT GCAGCCAAGC CCTTACGACA TATGGGCCAC
1561  CGCCGACCTG GTGGAGCTGG TTAAGCAGCG CATTGAGGTC ACGGATGGAA GGCTACAAGC
1621  GGCCTTTGTC GTGTCGCGGG CGATCAAAGG CACGCGCATC GGCGGTGAGG TTGCCGAGGC
1681  GCTGGCCGGG TACGAGCTGC CCATTCTTGA GTCCCGTATC ACGCAGCGCG TGAGCTACCC
1741  AGGCACTGCC GCCGCCGGCA CAACCGTTCT TGAATCAGAA CCCGAGGGCG ACGCTGCCCG
1801  CGAGGTCCAG GCGCTGGCCG CTGAAATTAA ATCAAAACTC ATTTGAGTTA ATGAGGTAAA
1861  GAGAAAATGA GCAAAAGCAC AAACACGCTA AGTGCCGGCC GTCCGAGCGC ACGCAGCAGC
1921  AAGGCTGCAA CGTTGGCCAG CCTGGCAGAC ACGCCAGCCA TGAAGCGGGT CAACTTTCAG
1981  TTGCCGGCGG AGGATCACAC CAAGCTGAAG ATGTACGCGG TACGCCAAGG CAAGACCATT
2041  ACCGAGCTGC TATCTGAATA CATCGCGCAG CTACCAGAGT AAATGAGCAA ATGAATAAAT
2101  GAGTAGATGA ATTTTAGCGG CTAAAGGAGG CGGCATGGAA AATCAAGAAC AACCAGGCAC
2161  CGACGCCGTG GAATGCCCCA TGTGTGGAGG AACGGGCGGT TGGCCAGGCG TAAGCGGCTG
2221  GGTTGTCTGC CGGCCCTGCA ATGGCACTGG AACCCCCAAG CCCGAGGAAT CGGCGTGAGC
2281  GGTCGCAAAC CATCCGGCCC GGTACAAATC GGCGCGGCGC TGGGTGATGA CCTGGTGGAG
2341  AAGTTGAAGG CCGCGCAGGC CGCCCAGCGG CAACGCATCG AGGCAGAAGC ACGCCCCGGT
2401  GAATCGTGGC AAGCGGCCGC TGATCGAATC CGCAAAGAAT CCCGGCAACC GCCGGCAGCC
2461  GGTGCGCCGT CGATTAGGAA GCCGCCCAAG GGCGACGAGC AACCAGATTT TTTCGTTCCG
2521  ATGCTCTATG ACGTGGGCAC CCGCGATAGT CGCAGCATCA TGGACGTGGC CGTTTTCCGT
2581  CTGTCGAAGC GTGACCGACG AGCTGGCGAG GTGATCCGCT ACGAGCTTCC AGACGGGCAC
2641  GTAGAGGTTT CCGCAGGGCC GGCCGGCATG GCCAGTGTGT GGGATTACGA CCTGGTACTG
2701  ATGGCGGTTT CCCATCTAAC CGAATCCATG AACCGATACC GGGAAGGGAA GGGAGACAAG
2761  CCCGGCCGCG TGTTCCGTCC ACACGTTGCG GACGTACTCA AGTTCTGCCG GCGAGCCGAT
2821  GGCGGAAAGC AGAAAGACGA CCTGGTAGAA ACCTGCATTC GGTTAAACAC CACGCACGTT
2881  GCCATGCAGC GTACGAAGAA GGCCAAGAAC GGCCGCCTGG TGACGGTATC CGAGGGTGAA
2941  GCCTTGATTA GCCGCTACAA GATCGTAAAG AGCGAAACCG GCGGCCGGA GTACATCGAG
3001  ATCGAGCTAG CTGATTGGAT GTACCGCGAG ATCACAGAAG GCAAGAACCC GGACGTGCTG
3061  ACGGTTCACC CCGATTACTT TTTGATCGAT CCCGGCATCG GCCGTTTTCT CTACCGCCTG
3121  GCACGCCGCG CCGCAGGCAA GGCAGAAGCC AGATGGTTGT TCAAGACGAT CTACGAACGC
3181  AGTGGCAGCG CCGGAGAGTT CAAGAAGTTC TGTTTCACCG TGCGCAAGCT GATCGGGTCA
3241  AATGACCTGC CGGAGTACGA TTTGAAGGAG GAGGCGGGGC AGGCTGGCCC GATCCTAGTC
3301  ATGCGCTACC GCAACCTGAT CGAGGGCGAA GCATCCGCCG GTTCCTAATG TACGGAGCAG
```

Figure 9

```
3361    ATGCTAGGGC AAATTGCCCT AGCAGGGGAA AAAGGTCGAA AAGGTCTCTT TCCTGTGGAT
3421    AGCACGTACA TTGGGAACCC AAAGCCGTAC ATTGGGAACC GGAACCCGTA CATTGGGAAC
3481    CCAAAGCCGT ACATTGGGAA CCGGTCACAC ATGTAAGTGA CTGATATAAA AGAGAAAAAA
3541    GGCGATTTTT CCGCCTAAAA CTCTTTAAAA CTTATTAAAA CTCTTAAAAC CCGCCTGGCC
3601    TGTGCATAAC TGTCTGGCCA GCGCACAGCC GAAGAGCTGC AAAAAGCGCC TACCCTTCGG
3661    TCGCTGCGCT CCCTACGCCC CGCCGCTTCG CGTCGGCCTA TCGCGGCCGC TGGCCGCTCA
3721    AAAATGGCTG GCCTACGCCC AGGCAATCTA CCAGGGCGCG GACAAGCCGC GCCGTCGCCA
3781    CTCGACCGCC GGCGCCCACA TCAAGGCACC CTGCCTCGCG CGTTTCGGTG ATGACGGTGA
3841    AAACCTCTGA CACATGCAGC TCCCGGAGAC GGTCACAGCT TGTCTGTAAG CGGATGCCGG
3901    GAGCAGACAA GCCCGTCAGG GCGCGTCAGC GGGTGTTGGC GGGTGTCGGG GCGCAGCCAT
3961    GACCCAGTCA CGTAGCGATA GCGGAGTGTA TACTGGCTTA ACTATGCGGC ATCAGAGCAG
4021    ATTGTACTGA GAGTGCACCA TATGCGGTGT GAAATACCGC ACAGATGCGT AAGGAGAAAA
4081    TACCGCATCA GGCGCTCTTC CGCTTCCTCG CTCACTGACT CGCTGCGCTC GGTCGTTCGG
4141    CTGCGGCGAG CGGTATCAGC TCACTCAAAG GCGGTAATAC GGTTATCCAC AGAATCAGGG
4201    GATAACGCAG GAAAGAACAT GTGAGCAAAA GGCCAGCAAA AGGCCAGGAA CCGTAAAAAG
4261    GCCGCGTTGC TGGCGTTTTT CCATAGGCTC CGCCCCCCTG ACGAGCATCA CAAAAATCGA
4321    CGCTCAAGTC AGAGGTGGCG AAACCCGACA GGACTATAAA GATACCAGGC GTTTCCCCCT
4381    GGAAGCTCCC TCGTGCGCTC TCCTGTTCCG ACCCTGCCGC TTACCGGATA CCTGTCCGCC
4441    TTTCTCCCTT CGGGAAGCGT GGCGCTTTCT CATAGCTCAC GCTGTAGGTA TCTCAGTTCG
4501    GTGTAGGTCG TTCGCTCCAA GCTGGGCTGT GTGCACGAAC CCCCCGTTCA GCCCGACCGC
4561    TGCGCCTTAT CCGGTAACTA TCGTCTTGAG TCCAACCCGG TAAGACACGA CTTATCGCCA
4621    CTGGCAGCAG CCACTGGTAA CAGGATTAGC AGAGCGAGGT ATGTAGGCGG TGCTACAGAG
4681    TTCTTGAAGT GGTGGCCTAA CTACGGCTAC ACTAGAAGGA CAGTATTTGG TATCTGCGCT
4741    CTGCTGAAGC CAGTTACCTT CGGAAAAAGA GTTGGTAGCT CTTGATCCGG CAAACAAACC
4801    ACCGCTGGTA GCGGTGGTTT TTTTGTTTGC AAGCAGCAGA TTACGCGCAG AAAAAAAGGA
4861    TCTCAAGAAG ATCCTTTGAT CTTTTCTACG GGGTCTGACG CTCAGTGGAA CGAAAACTCA
4921    CGTTAAGGGA TTTTGGTCAT GCATGATATA TCTCCCAATT TGTGTAGGGC TTATTATGCA
4981    CGCTTAAAAA TAATAAAAGC AGACTTGACC TGATAGTTTG GCTGTGAGCA ATTATGTGCT
5041    TAGTGCATCT AACGCTTGAG TTAAGCCGCG CCGCGAAGCG GCGTCGGCTT GAACGAATTT
5101    CTAGCTAGAC ATTATTTGCC GACTACCTTG GTGATCTCGC CTTTCACGTA GTGGACAAAT
5161    TCTTCCAACT GATCTGCGCG CGAGGCCAAG CGATCTTCTT CTTGTCCAAG ATAAGCCTGT
5221    CTAGCTTCAA GTATGACGGG CTGATACTGG GCCGGCAGGC GCTCCATTGC CCAGTCGGCA
5281    GCGACATCCT TCGGCGCGAT TTTGCCGGTT ACTGCGCTGT ACCAAATGCG GACAACGTA
5341    AGCACTACAT TTCGCTCATC GCCAGCCCAG TCGGCGGCG AGTTCCATAG CGTTAAGGTT
5401    TCATTTAGCG CCTCAAATAG ATCCTGTTCA GGAACCGGAT CAAAGAGTTC CTCCGCCGCT
5461    GGACCTACCA AGGCAACGCT ATGTTCTCTT GCTTTTGTCA GCAAGATAGC CAGATCAATG
5521    TCGATCGTGG CTGGCTCGAA GATACCTGCA AGAATGTCAT TGCGCTGCCA TTCTCCAAAT
5581    TGCAGTTCGC GCTTAGCTGG ATAACGCCAC GGAATGATGT CGTCGTGCAC AACAATGGTG
5641    ACTTCTACAG CGCGGAGAAT CTCGCTCTCT CCAGGGGAAG CCGAAGTTTC CAAAAGGTCG
5701    TTGATCAAAG CTCGCCGCGT TGTTTCATCA AGCCTTACGG TCACCGTAAC CAGCAAATCA
5761    ATATCACTGT GTGGCTTCAG GCCGCCATCC ACTGCGGAGC CGTACAAATG TACGGCCAGC
5821    AACGTCGGTT CGAGATGGCG CTCGATGACG CCAACTACCT CTGATAGTTG AGTCGATACT
5881    TCGGCGATCA CCGCTTCCCC CATGATGTTT AACTTTGTTT TAGGGCGACT GCCCTGCTGC
5941    GTAACATCGT TGCTGCTCCA TAACATCAAA CATCACCCA CGGCGTAACG CGCTTGCTGC
6001    TTGGATGCCC GAGGCATAGA CTGTACCCCA AAAAAACAGT CATAACAAGC CATGAAAACC
6061    GCCACTGCGC CGTTACCACC GCTGCGTTCG GTCAAGGTTC TGGACCAGTT GCGTGACGGC
6121    AGTTACGCTA CTTGCATTAC AGCTTACGAA CCGAACGAGG CTTATGTCCA CTGGGTTCGT
6181    GCCCGAATTG ATCACAGGCA GCAACGCTCT GTCATCGTTA CAATCAACAT GCTACCCTCC
6241    GCGAGATCAT CCGTGTTTCA AACCCGGCAG CTTAGTTGCC GTTCTTCCGA ATAGCATCGG
6301    TAACATGAGC AAAGTCTGCC GCCTTACAAC GGCTCTCCCG CTGACGCCGT CCCGGACTGA
6361    TGGGCTGCCT GTATCGAGTG GTGATTTTGT GCCGAGCTGC CGGTCGGGGA CTGTTGGCT
6421    GGCTGGTGGC AGGATATATT GTGGTGTAAA CAAATTGACG CTTAGACAAC TTAATAACAC
6481    ATTGCGGACG TTTTAATGT ACTGAATTAA CGCCGAATTG CTCTAGCATT CGCCATTCAG
6541    GCTGCGCAAC TGTTGGGAAG GGCGATCGGT GCGGGCCTCT TCGCTATTAC GCCAGCTGGC
6601    GAAAGGGGGA TGTGCTGCAA GGCGATTAAG TTGGGTAACG CCAGGGTTTT CCCAGTCACG
6661    ACGTTGTAAA ACGACGGCCA GTGCCAAGCT AATTCGCTTC AAGACGTGCT CAAATCACTA
6721    TTTCCACACC CCTATATTTC TATTGCACTC CCTTTTAACT GTTTTTATT ACAAAAATGC
```

Figure 9 cont.

```
6781  CCTGGAAAAT GCACTCCCTT TTTGTGTTTG TTTTTTTGTG AAACGATGTT GTCAGGTAAT
6841  TTATTTGTCA GTCTACTATG GTGGCCCATT ATATTAATAG CAACTGTCGG TCCAATAGAC
6901  GACGTCGATT TTCTGCATTT GTTTAACCAC GTGGATTTTA TGACATTTTA TATTAGTTAA
6961  TTTGTAAAAC CTACCCAATT AAAGACCTCA TATGTTCTAA AGACTAATAC TTAATGATAA
7021  CAATTTTCTT TTAGTGAAGA AAGGGATAAT TAGTAAATAT GGAACAAGGG CAGAAGATTT
7081  ATTAAAGCCG CGGTAAGAGA CAACAAGTAG GTACGTGGAG TGTCTTAGGT GACTTACCCA
7141  CATAACATAA AGTGACATTA ACAAACATAG CTAATGCTCC TATTTGAATA GTGCATATCA
7201  GCATACCTTA TTACATATAG ATAGGAGCAA ACTCTAGCTA GATTGTTGAG CAGATCTCGG
7261  TGACGGGCAG GACCGGACGG GGCGGTACCG GCAGGCTGAA GTCCAGCTGC CAGAAACCCA
7321  CGTCATGCCA GTTCCCGTGC TTGAAGCCGG CCGCCCGCAG CATGCCGCGG GGGGCATATC
7381  CGAGCGCCTC GTGCATGCGC ACGCTCGGGT CGTTGGGCAG CCCGATGACA GCGACCACGC
7441  TCTTGAAGCC CTGTGCCTCC AGGGACTTCA GCAGGTGGGT GTAGAGCGTG GAGCCCAGTC
7501  CCGTCCGCTG GTGGCGGGGG GAGACGTACA CGGTCGACTC GGCCGTCCAG TCGTAGGCGT
7561  TGCGTGCCTT CCAGGGGCCC GCGTAGGCGA TGCCGGCGAC CTCGCCGTCC ACCTCGGCGA
7621  CGAGCCAGGG ATAGCGCTCC CGCAGACGGA CGAGGTCGTC CGTCCACTCC TGCGGTTCCT
7681  GCGGCTCGGT ACGGAAGTTG ACCGTGCTTG TCTCGATGTA GTGGTTGACG ATGGTGCAGA
7741  CCGCCGGCAT GTCCGCCTCG GTGGCACGGC GGATGTCGGC CGGGCGTCGT TCTGGGCTCA
7801  TGGTAGATCC CCCGTTCGTA AATGGTGAAA ATTTTCAGAA AATTGCTTTT GCTTTAAAAG
7861  AAATGATTTA AATTGCTGCA ATAGAAGTAG AATGCTTGAT TGCTTGAGAT TCGTTTGTTT
7921  TGTATATGTT GTGTTGAGAA TTAATTCTCG AGGTCCTCTC CAAATGAAAT GAACTTCCTT
7981  ATATAGAGGA AGGGTCTTGC GAAGGATAGT GGGATTGTGC GTCATCCCTT ACGTCAGTGG
8041  AGATATCACA TCAATCCACT TGCTTTGAAG ACGTGGTTGG AACGTCTTCT TTTTCCACGA
8101  TGCTCCTCGT GGGTGGGGGT CCATCTTTGG GACCACTGTC GGTAGAGGCA TCTTGAACGA
8161  TAGCCTTTCC TTTATCGCAA TGATGGCATT TGTAGGAGCC ACCTTCCTTT TCCACTATCT
8221  TCACAATAAA GTGACAGATA GCTGGGCAAT GGAATCCGAG GAGGTTTCCG GATATTACCC
8281  TTTGTTGAAA AGTCTCAATT GCCCTTTGGT CTTCTGAGAC TGTATCTTTG ATATTTTTGG
8341  AGTAGACAAG TGTGTCGTGC TCCACCATGT TATCACATCA ATCCACTTGC TTTGAAGACG
8401  TGGTTGGAAC GTCTTCTTTT TCCACGATGC TCCTCGTGGG TGGGGGTCCA TCTTTGGGAC
8461  CACTGTCGGC AGAGGCATCT TCAACGATGG CCTTTCCTTT ATCGCAATGA TGGCATTTGT
8521  AGGAGCCACC TTCCTTTTCC ACTATCTTCA CAATAAAGTG ACAGATAGCT GGGCAATGGA
8581  ATCCGAGGAG GTTTCCGGAT ATTACCCTTT GTTGAAAAGT CTCAATTGCC CTTTGGTCTT
8641  CTGAGACTGT ATCTTTGATA TTTTTGGAGT AGACAAGTGT GTCGTGCTCC ACCATGTTGA
8701  CCTGCAGGCA TGCAAGCTTG CATGCCTGCA GGTCGACTCT AGAGGATCCC CGGGTACCGA
8761  GCTCGAATTC GTAATCATGT CATAGCTGTT TCCTGTGTGA AATTGTTATC CGCTCACAAT
8821  TCCACACAAC ATACGAGCCG GAAGCATAAA GTGTAAAGCC TGGGGTGCCT AATGAGTGAG
8881  CTAACTCACA TTAATTGCGT TGCGCTCACT GCCCGCTTTC CAGTCGGGAA ACCTGTCGTG
8941  CCAGCTGCAT TAATGAATCG GCCAACGCGC GGGGAGAGGC GGTTTGCGTA TTGGAGCTTG
9001  AGCTTGGATC AGATTGTCGT TTCCCGCCTT CAGTTTAAAC TATCAGTGTT TGACAGGATA
9061  TATTGGCGGG TAAACCTAAG AGAAAAGAGC GTTTATTAGA ATAATCGGAT ATTTAAAAGG
9121  GCGTGAAAAG GTTTATCCGT TCGTCCATTT GTATGTGCAT GCCAACCACA GGGTTCCCCT
9181  CGGGATCAA
```

Figure 9 cont.

```
XvPsap1D    ACTGTCTGGGTAGCTGGCAATATAGAGACGTAAATAATTGTCTGTAAATAGGGAGAAATT    60
XvPsap1E    ACTGTCTGGGTAGCTGGCAATATAGAGACGTAAATAATTGTCTGTAAATAGGGAGAAATT    60
XvPsap1G    ACTGTCTGGGTAGCTGGCAATATAGAGACGTAAATAATTGTCTGTAAATAGGGAGAAATT    60
Consensus   actgtctgggtagctggcaatatagagacgtaaataattgtctgtaaatagggagaaatt XvPsap1D    CATGGATCATCACCCTAATTCGGTCTTTCACTCATTTTATCATAGACCTGACTAAAGAAC   120
XvPsap1E    CATGGATCATCACCCTAATTCGGTCTTTCACTCATTTTATCATAGACCTGACTAAAGAAC   120
XvPsap1G    CATGGATCATCACCCTAATTCGGTCTTTCACTCATTTTATCATAGACCTGACTAAAGAAC   120
Consensus   catggatcatcaccctaattcggtcttcactcattttatcatagacctgactaaagaac XvPsap1D    TTGGTCAGAGTTTTTACTTATTTAAAATAAAGAGGACTTCATGGCATCCATGTGCAGGTA   180
XvPsap1E    TTGGTCAGAGTTTTTACTTATTTAAAATAAAGAGGACTTCATGGCATCCATGTGCAGGTA   180
XvPsap1G    TTGGTCAGAGTTTTTACTTATTTAAAATAAAGAGGACTTCATGGCATCCATGTGCAGGTA   180
Consensus   ttggtcagagtttttacttatttaaaataaagaggacttcatggcatccatgtgcaggta XvPsap1D    CAGCTCCCAGAAAAAAAGCATGAAACACGAGAGGATCAATAGCATTCGATCTGAAACAA   240
XvPsap1E    CAGCTCCCAGAAAAAAAGCATGAAACACGAGAGGATCAATAGCATTCGATCTGAAACAA   240
XvPsap1G    CAGCTCCCAGAAAAAAAGCATGAAACACGAGAGGATCAATAGCATTCGATCTGAAACAA   240
Consensus   cagctcccagaaaaaaagcatgaaacacgagaggatcaatagcattcgatctgaaacaa XvPsap1D    AAGGTTGCAGCTCAAGACTTTCTCCAAAATATTAAGATGATCCAAAGAATTACCCCAAGA   300
XvPsap1E    AAGGTTGCAGCTCAAGACTTTCTCCAAAATATTAAGATGATCCAAAGAATTACCCCAAGA   300
XvPsap1G    AAGGTTGCAGCTCAAGACTTTCTCCAAAATATTAAGATGATCCAAAGAATTACCCCAAGA   300
Consensus   aacgttgcagctcaag............aatattaagatgatccaaagaattaccccaaga XvPsap1D    TATCCAACGTATACCAATGTGTATACCGAAAGTAAGAAAGTTCACGTGCATTCTTTGATT   360
XvPsap1E    TATCCAACGTATACCAATGTGTATACCGAAAGTAAGAAAGTTCACGTGCAT.........   351
XvPsap1G    TATCCAACGTATACCAATGTGTATACCGAAAGTAAGAAAGTTCACGTGCAT.........   351
Consensus   tatccaacgtataccaatgtgtataccgaaagtaagaaagttcacgtgcattctttgatt XvPsap1D    TTTCTCCCGAGTGTTCTTTTCTGAAATGAGTAAATAAGACTAGAATAAGAGCTAATGTAT   420
XvPsap1E    ............................................................   351
XvPsap1G    ............................................................   351
Consensus   tttctcccgagtgttcttttctgaaatgagtaaataagactagaataagagctaatgtat XvPsap1D    TTTTTTTCTAAAAAAAGTTGAATGTGGATACAATATGATTATACATTCATTAGCTATTTT   480
XvPsap1E    ............................................................   351
XvPsap1G    ............................................................   351
Consensus   tttttttctaaaaaaagttgaatgtggatacaatatgattatacattcattagctatttt XvPsap1D    AAGTATATTCTATTTTTTTTCCCCCCAAAAGAACACAAATGTGTTCCGTCACTTTCCATG   540
XvPsap1E    ............................................................   351
XvPsap1G    ............................................................   351
Consensus   aagtatattctatttttttccccccaaaagaacacaaatgtgttccgtcactttccatg XvPsap1D    TCTTAGAATTGGACAGGGTGCTTATGATACAACTTGTTCCTATCAACAACTGCATGTTAG   600
XvPsap1E    TCTTAGAATTGGACAGGGTGCTTATGATACAACTTGTTCCTATCAACAACTGCATGTTAG   411
XvPsap1G    ............................................................   351
Consensus   tcttagaattggacagggtgcttatgatacaacttgttcctatcaacaactgcatgttag XvPsap1D    ACAGCGCCGAATTTACAGTCCTACTGGGCGCCACTTTTCAACCCACATCATCAAGATGAA   660
XvPsap1E    ACAGCGCCGAATTTACAGTCCTACTGGGCGCCACTTTTCAACCCACATCATCAAGATGAA   471
XvPsap1G    ............................................................   351
Consensus   acagcgccgaatttacagtcctactgggcgccacttttcaacccacatcatcaagatgaa
```

Figure 15

```
XvPsap1D    CACCACGTTATCTTCATCCGCTCCAACCACATGGTCCAGCGCCACTGGCCAAGACCGCCA    720
XvPsap1E    CACCACGTTATCTTCATCCGCTCCAACCACATGGTCCAGCGCCACTGGCCAAGACCGCCA    531
XvPsap1G    ............................................................    351
Consensus   caccacgttatcttcatccgctccaaccacatggtccagcgccactggccaagaccgcca XvPsap1D    GCCAGCCAGGCCATCCAACGTGGTGCATTTTCTAACACTCCACGTTCGCTGTACGGCATT    780
XvPsap1E    GCCAGCCAGGCCATCCAACGTGGTGCATTTTCTAACACTCCACGTTCGCTGTACGGCATT    591
XvPsap1G    ................ACGTGGTGCATTTTCTAACACTCCACGTTCGCTGTACGGCATT    394
Consensus   gccagccaggccatccaacgtggtgca            actccacgttcgctgtacggcatt XvPsap1D    ATTTCTCCAGCCAGAAAGACCGAGACAGCGACGCTGTTGGGCGGGCCCGCGGCCTGCTCT    840
XvPsap1E    ATTTCTCCAGCCAGAAAGACCGAGACAGCGACGCTGTTGGGCGGGCCCGCGGCCTGCTCT    651
XvPsap1G    ATTTCTCCAGCCAGAAAGACCGAGACAGCGACGCTGTTGGGCGGGCCCGCGGCCTGCTCT    454
Consensus   atttctccagccagaaagaccgagacagcgacgctgttgggcgggcccgcggcctgctct XvPsap1D    CTCTGCTTCCCCATGAGATTCACGGGCATCGCTCCTCGCTCGTGCCTACGCGACCGCGCC    900
XvPsap1E    CTCTGCTTCCCCATGAGATTCACGGGCATCGCTCCTCGCTCGTGCCTACGCGACCGCGCC    711
XvPsap1G    CTCTGCTTCCCCATGAGATTCACGGGCATCGCTCCTCGCTCGTGCCTACGCGACCGCGCC    514
Consensus   ctctgcttccccatgagattcacgggcatcgctcctcgctcgtgcctacgcgaccgcgcc XvPsap1D    GATCCACGTG ACGTGGCGCAGCAATCGTTCTTACTAGGCGCTTGCACGTGTCGTTCGCAT    960
XvPsap1E    GATCCACGTG ACGTGGCGCAGCAATCGTTCTTACTAGGCGCTTGCACGTGTCGTTCGCAT    771
XvPsap1G    GATCCACGTG ACGTGGCGCAGCAATCGTTCTTACTAGGCGCTTGCACGTGTCGTTCGCAT    574
Consensus   gatc cacgtg  acgtggc gcagcaatcgttcttactaggcgct tgcacgtgtc gttcgcat XvPsap1D    GCGAAGCGTCCACACTGCCAACGACCTCCTTAAATATCCTTGTGATATTCGCCTTACGAT    1020
XvPsap1E    GCGAAGCGTCCACACTGCCAACGACCTCCTTAAATATCCTTGTGATATTCGCCTTACGAT    831
XvPsap1G    GCGAAGCGTCCACACTGCCAACGACCTCCTTAAATATCCTTGTGATATTCGCCTTACGAT    634
Consensus   gcgaagcgtccacactgccaacgacctccttaaatatccttgtgatattcgccttacgat XvPsap1D    CTCACACTTCGCACGCAAAGGCCAGTCGCAGATTTGGGTTGAATTTGCTGCGTTTTGGCA    1080
XvPsap1E    CTCACACTTCGCACGCAAAGGCCAGTCGCAGATTTGGGTTGAATTTGCTGCGTTTTGGCA    891
XvPsap1G    CTCACACTTCGCACGCAAAGGCCAGTCGCAGATTTGGGTTGAATTTGCTGCGTTTTGGCA    694
Consensus   ctcacacttcgcacgcaaaggccagtcgcagatttgggttgaatttgctgcgttttggca XvPsap1D    GATTTGAGCGAGAGATATTAGGGAAG    1107
XvPsap1E    GATTTGAGCGAGAGATATTAGGGAAG    918
XvPsap1G    GATTTGAGCGAGAGATATTAGGGAAG    721
Consensus   gattttgagcgagagatattagggaag
```

Figure 15 cont.

STRESS INDUCIBLE DERIVATIVE PROMOTER

REFERENCE TO SEQUENCE LISTING SUBMITTED ELECTRONICALLY

The official copy of the sequence listing is submitted electronically via EFS-Web as an ASCII-formatted sequence listing with a file named "3000012-001000_Sub_Seq_Listing.ST25.txt" created on Jul. 20, 2015, and having a size of 34 kilobytes. The sequence listing contained in this ASCII-formatted document is part of the specification and is herein incorporated by reference in its entirety.

CROSS REFERENCE TO RELATED APPLICATIONS

This application is a §371 National Stage Application of PCT/IB2013/058399, filed Sep. 9, 2013, which claims priority to ZA 2012/06750, filed Sep. 10, 2012.

BACKGROUND

Field of the Invention

This invention relates to a derivative plant promoter inducible by abiotic stress, and host cells and transgenic plants transformed with the abiotic stress-inducible promoter.

Description of Related Art

Abiotic stresses include drought, salinity and extreme temperatures. These stresses, particularly drought, cause extensive losses to agricultural crop production. The ability of crop plants to tolerate drought conditions would be beneficial in reducing these losses.

A plant promoter inducible under abiotic stress conditions is described in PCT/IB2008/054628 (published as WO2009/060402), the contents of which are incorporated by reference. On the whole, in comparison to the high level transgene expression by constitutive promoters, stress-inducible promoters provide poor expression levels of genes in transgenic plants. On the other hand, the stress-inducible promoter, XvPSap1, isolated from the genome of a desiccation tolerant monocotyledonous plant, *Xerophyta viscosa*, was found to express efficiently. However, the XvPSap1, promoter has a disadvantage in that the sequence is relatively large. The large promoter size is a limiting factor for its use in the development of transgenic plants, as the longer the transgenic DNA sequence, the lower the efficiency of transformation and stability of the trait. As such, this will greatly limit the use of XvPSap1 in biotechnological applications.

A need therefore exists for an abiotic stress-inducible promoter that can be used to transform crop plants and which has a shorter length than XvPSap1, but is still able to function at least as well as XvPSap1.

SUMMARY OF THE INVENTION

According to a first embodiment of the invention, there is provided an isolated derivative plant promoter nucleotide sequence from *Xerophyta viscosa* which functions as a plant promoter inducible by abiotic stress.

The nucleotide sequence may be derived from *Xerophyta viscosa* XvPSap1 or may be artificially synthesised.

The derivative promoter fragment nucleotide sequence may comprise any one or more of the regulatory elements identified as: TC-rich repeats ▓▓▓▓▓ (SEQ ID NO: 31), ▓▓▓▓▓ (SEQ ID NO: 32); MYB transcription factor binding site caatg (SEQ ID NO: 33); or ABA-responsive elements ▓▓▓▓ (SEQ ID NO: 34), ▓▓▓▓ (SEQ ID NO: 34), ▓▓▓▓ (SEQ ID NO: 35), ▓▓▓▓▓ (SEQ ID NO: 36) as illustrated in FIG. 15.

The nucleotide sequence may be:
(a) a nucleic acid sequence that exhibits at least 80% sequence identity to any one of SEQ ID NO:1 to 3 (FIGS. 1 to 3); or
(b) a sequence which hybridises under stringent conditions to the reverse complement of any one of SEQ ID NO:1 to 3 (FIGS. 4 to 6); or
(c) a nucleic acid sequence of any one of SEQ ID NOs: 1-3.

Preferably, the derivative promoter functions as an abiotic stress inducible promoter.

More preferably, the nucleotide sequence may have at least 85%, 90%, or 95% identity to any one of SEQ ID NO:1 to 3 (FIGS. 1 to 3).

Even more preferably, the nucleotide sequence may be any one of SEQ ID NO:1 to 3 (FIGS. 1 to 3) or a sequence which hybridises under stringent conditions to the reverse complement of any one of SEQ ID NO:1 to 3 (FIGS. 4 to 6) and functions as an abiotic stress inducible promoter.

The abiotic stress may be osmotic stress, dehydration stress, drought, salinity, desiccation or extreme temperatures.

Hybridisation may occur under stringent conditions that include a wash in 0.1 SSC at about 60° C. to about 65° C.

According to a further embodiment of the invention, there is provided a nucleotide cassette comprising the promoter fragment of the invention.

According to a further embodiment of the invention, there is provided a recombinant plant vector comprising the promoter fragment of the invention.

The nucleotide cassette or plant vector may further comprise a heterologous transcribable DNA sequence. According to one embodiment of the invention the heterologous transcribable DNA sequence, operably linked to the promoter, may be a gene enconding a polypeptide of interest. For example, the gene may be an abiotic stress tolerance gene which when expressed by the promoter in a plant provides tolerance to an abiotic stress. More preferably, the gene may be XvSap1, XvPrx2, Xvper1, XvAld or any other gene providing tolerance to an abiotic stress known to those skilled in the art.

In an alternative embodiment of the invention, the gene is any gene desired to be inducibly expressed in a plant by an abiotic stress. The gene may be a plant gene or a foreign gene, such as an animal, bacterial, fungal or viral gene.

In yet another embodiment of the invention the heterologous transcribable DNA sequence includes a polynucleotide sequence of interest which is transcribed into a functional RNA, such as a shRNA, miRNA, siRNA, mRNA or the like.

The recombinant plant vector may be a T-derived plasmid construct of *Agrobacterium tumefaciens*.

According to a further embodiment of the invention, there is provided a host cell into which the nucleotide cassette or plant vector has been transformed.

The host cell may be a plant cell.

According to a further embodiment of the invention, there is provided a transgenic plant or plant part transformed with the minimal plant promoter fragment of the invention and a gene operably linked to the minimal plant promoter fragment of the invention. For example, the gene may be an abiotic stress tolerance gene which when expressed in the transgenic plant or plant part provides tolerance to an abiotic stress. More preferably, the gene may be XvSap1, XvPrx2, XvPer1, XvAld or any other gene providing tolerance to an abiotic stress known to those skilled in the art.

In an alternative embodiment of the invention, the gene is any gene desired to be inducibly expressed in the transgenic plant or plant part by an abiotic stress. The gene may be a plant gene, including a plant gene suitable for providing tolerance to an abiotic stress known to those skilled in the art, including, but not limited to, XvSap1, XvPrx2, XvPer1 or XvAld, or the gene may be a foreign gene, such as an animal, bacterial, fungal or viral gene.

The transgenic plant may be a monocotyledonous or dicotyledonous plant, such as maize, tobacco, sorghum, wheat, cassava, barley, oats, rye, sweet potatoes, soybean, alfalfa, tobacco, sunflower, cotton, canola and the like.

The transgenic plant part may be selected from the group consisting of: cells, protoplasts, cell tissue cultures, callus, cell crumps, embryos, pollen, ovules, seeds, flowers, kernels, ears, cobs, leaves, husks, stalks, roots, root tips, anthers, seeds and silk.

According to a further embodiment of the invention, there is provided a method for enhancing the stress tolerance of a plant by introducing the minimal promoter fragment of the invention operably linked to an abiotic stress tolerance gene under control of the promoter which, when expressed in a transgenic plant or plant part, provides tolerance to an abiotic stress. For example, the gene may be XvSap1, XvPrx2, Xvper1, XvAld or any other gene providing tolerance to an abiotic stress known to those skilled in the art.

In yet another embodiment of the invention, there is provided for methods of regulation of transcription of heterologous transcribable DNA sequences either in a host cell or a transgenic plant.

A further embodiment incorporates producing a transgenic plant by transforming a plant cell with a nucleotide cassette as described herein and regenerating a plant from the transformed cell.

BRIEF DESCRIPTION OF THE DRAWINGS

FIG. 1: shows the nucleotide sequence for XvPSap1D (SEQ ID NO:1).

FIG. 2: shows the nucleotide sequence for XvPSap1E (SEQ ID NO:2).

FIG. 3: shows the nucleotide sequence for XvPSap1G (SEQ ID NO:3).

FIG. 4: shows the reverse complement nucleotide sequence for XvPSap1D (SEQ ID NO:4).

FIG. 5: shows the reverse complement nucleotide sequence for XvPSap1E (SEQ ID NO:5).

FIG. 6: shows the reverse complement nucleotide sequence for XvPSap1G (SEQ ID NO:6).

FIG. 7: shows the nucleotide sequence of the luc gene (SEQ ID NO:10).

FIG. 8: shows the nucleotide sequence of NosT (SEQ ID NO:11).

FIG. 9: shows the nucleotide sequence of the pTF101.1 vector (SEQ ID NO:29).

FIG. 15: Alignment of XvPsap1D (SEQ ID NO: 1), XvPsap1E (SEQ ID NO: 2) and XvPsap1G (SEQ ID NO: 3), and the Consensus (SEQ ID NO: 30) showing putative regulatory elements in the minimal XvPsap1 promoters. Key: TC-rich repeats:  (SEQ ID NO: 31), 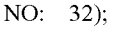 (SEQ ID NO: 32); MYB binding site: caactg (SEQ ID NO: 33); ABRE:  (SEQ ID NO: 34), 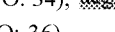 (SEQ ID NO: 34), 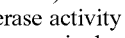 (SEQ ID NO: 35),  (SEQ ID NO: 36).

DETAILED DESCRIPTION OF A PREFERRED EMBODIMENT

Figure 10:
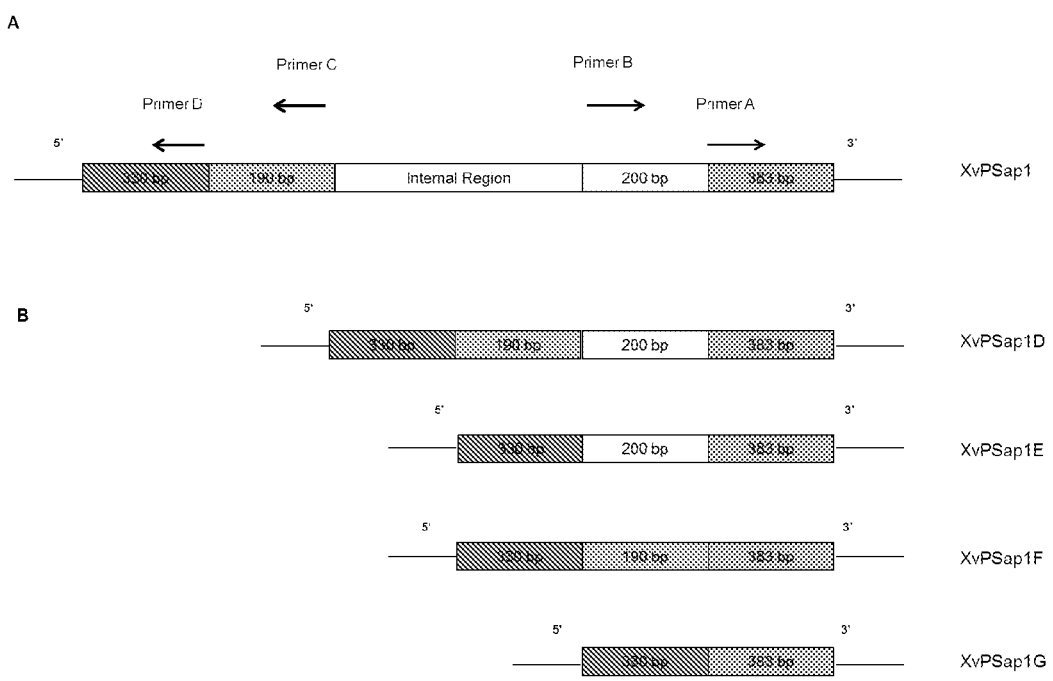
FIG. 10: shows a graphical illustration of the minimal XvPSap1 promoter fragments in comparison to full length XvPSap1.

The present invention will now be described more fully hereinafter with reference to the accompanying figures, in which some, but not all embodiments of the invention are shown.

The invention as described should not to be limited to the specific embodiments disclosed and modifications and other embodiments are intended to be included within the scope of the invention. Although specific terms are employed herein, they are used in a generic and descriptive sense only and not for purposes of limitation.

Terms used herein have their ordinary meaning recognised in the art unless otherwise indicated.

The present invention provides for polynucleotides having gene regulatory activity and which are derived from the XvPSap1 (SEQ ID NO:9) promoter of the monocotyledenous plant *Xerophyta viscosa*. The derivative promoter fragments of the invention display regulatory activity and are inducible by abiotic stress. The present invention also relates to host cells and transgenic plants transformed with the abiotic stress-inducible promoter fragments.

In comparison to the high level transgene expression by constitutive promoters, stress-inducible promoters result in relatively low expression levels in transgenic plants. For example, the XvPSap1 abiotic stress-inducible promoter has efficient expression levels, but due to the large size of the promoter, its use is problematic in the development of transgenic plants. Previous attempts to improve on the XvPSap1 promoter and generate shorter promoter fragments which are functionally active were focussed on producing 5' truncated promoter fragments to regulate expression of the reporter genes in tobacco and Black Mexican Sweetcorn (BMS) cells under dehydration. These 5' promoter fragments displayed significantly lower levels of expression than the full length XVPsap1 promoter (Oduor et al., 2009). Due to their attenuated functionality, 5' promoter fragments of the XvPSap1 promoter have limited commercial use and/or biological functionality.

Surprisingly, however, when mutagenesis studies producing internal deletions within the XvPSap1 promoter to produce the derivative promoter fragments of the invention, three of the four derivative promoter fragments, herein designated, XvPSap1D (SEQ ID NO:1), XvPSap1E (SEQ ID NO:2), and XvPSap1G (SEQ ID NO:3) (FIGS. 1 to 3), elicited high levels of gene expression, at least equivalent to the full-length XvPSap1 promoter, without adversely affecting plant growth. The derivative promoter fragments of the present invention are approximately 50% shorter than the full length XvPSap1 promoter and share only 40 to 50% sequence identity with the full length promoter. The three promoter fragments share 83% sequence identity with each other. Therefore, it is envisaged that nucleotide sequences within 83% of any of the XvPSap1D, XvPSap1E, and XvPSap1G promoter fragment sequences would be functional and elicit high level gene expression.

As used herein, "percent (%) sequence identity" with respect to the XvPSap1D, XvPSap1E and XvPSap1G sequences is defined as the percentage of nucleotides in a candidate sequence that are identical to the nucleotides in the sequences of XvPSap1D, XvPSap1E or XvPSap1G, respectively, after aligning the sequences and introducing gaps, if necessary, to achieve a maximum percent sequence identity. Alignment for purposes of determining percent sequence identity can be achieved in various ways that are within the knowledge of those with skill in the art. These ways may include, for instance, using computer software such as ALIGN, Megalign (DNASTAR), CLUSTALW or BLAST software. Those skilled in the art can determine appropriate parameters for measuring alignment, including any algorithms needed to achieve maximal alignment over the full length of the sequences being compared.

In one embodiment of the invention there is provided for a polynucleotide sequence that has at least about 80% sequence identity, at least about 90% sequence identity, or even greater sequence identity, such as about 95%, about 96%, about 97%, about 98% or about 99% sequence identity to the derivative promoter sequences, being XvPSap1D, XvPSap1E or XvPSap1G, described herein. Accordingly, polynucleotide sequences that are capable of regulating the transcription of an operably linked polynucleotide sequence and which have a greater than 80% sequence identity to the XvPSap1D, XvPSap1E and XvPSap1D polynucleotide sequences of the invention, are encompassed within the scope of this invention.

The invention also encompasses polynucleotide sequences capable of hybridising to a reverse complementary sequence of any of the XvPSap1D, XvPSap1E, and XvPSap1G derivative promoter fragment sequences under stringent conditions (FIGS. 4 to 6). The "stringency" of a hybridisation reaction is readily determinable by one of ordinary skill in the art, and generally is an empirical calculation which depends upon probe length, washing temperature, and salt concentration. In general, longer probes required higher temperatures for proper annealing, while shorter probes require lower temperatures. Hybridisation generally depends on the ability of denatured DNA to re-anneal when complementary strands are present in an environment below their melting temperature. A typical example of such "stringent" hybridisation conditions would be hybridisation carried out for 18 hours at 65° C. with gentle shaking, a first wash for 12 min at 65° C. in Wash Buffer A (0.5% SDS; 2×SSC), and a second wash for 10 min at 65° C. in Wash Buffer B (0.1% SDS; 0.5% SSC).

The XvPSap1D, XvPSap1E, and XvPSap1G promoter fragments are inserted upstream of an operably linked heterologous transcribable DNA sequence and this construct is cloned into a vector. It will be appreciated that the promoter fragment and the heterologous transcribable DNA sequence may be sequentially cloned into the vector. In this conformation the promoter fragments are operably linked to the relevant heterologous transcribable DNA sequence and may inducibly regulate the transcription of the heterologous transcribable DNA sequence. It will be readily apparent to those of skill in the art what the requirements are for a vector for use in the transformation of plants. Those of skill in the art will also appreciate that certain components may also be introduced into the vector including, but not limited to, 3' untranslated regions, such as terminators; 5' untranslated regions, such as regulatory elements; enhancers; introns; signal peptides; transit peptides; and other components. The vector may then then be introduced into a plant using any of the methods of plant transformation known to those of skill in the art in order to produce a transgenic plant. A "transgenic plant" refers to a plant or its progeny, wherein the DNA of the plant contains an exogenous DNA fragment which has been stably introduced into the plant and wherein the exogenous DNA is heritable.

The heterologous transcribable DNA sequences which are under the control of the derivative promoter fragments of the invention may include polynucleotide sequences encoding polypeptides or polynucleotide sequences which are translated into functional RNAs.

Heterologous transcribable DNA sequences encoding polypeptides of interest which may be inducibly expressed under control of the derivative plant promoters include, but are not limited to, genes that confer desirable characteristics to the transformed plant and/or genes which encode polypeptides of economic importance. Preferably the transgenes under the control of the promoter fragments of the invention may encode polypeptides, including but not limited to: abiotic stress tolerance proteins; antibodies; biofuels; biopolymers; industrial enzymes; pharmaceutical polypeptides; proteins which affect the ripening of fruit, proteins which provide improved nutritional content, including proteins affecting the yields of for instance fatty acids, oils, proteins and/or starches; proteins affecting resistance, including for instance bacterial resistance proteins, fungal resistance proteins, herbicide resistance proteins, insect resistance proteins, nematode resistance proteins, or viral resistance proteins. Alternatively, the heterologous transcribable DNA sequence may be translated into an RNA molecule such as a regulatory RNA, including for instance a miRNA, siRNA, antisense RNA or the like. Upon subjecting the transgenic plant to an abiotic stress, including drought, salinity, temperature stress, dessication, osmotic stress or dessicataion the heterologous transcribable DNA sequence is expressed under the control of the derivative promoter fragment. It is envisioned that any polynucleotide sequence that encodes a polypeptide or mRNA that expresses a phenotype or change in morphology may be useful in the practice of the present invention.

In a preferred embodiment of the invention, there is provided for the production of transgenic plants tolerant to abiotic stresses, such transgenic plants include transgenes under the control of the inducible promoter fragments of the invention such as XvSap1, XvPrx2, XyPer1, or XvAld (Garwe et al., 2003, Garwe et al., 2007, Iyer et al., 2007 and Bhatnagar-Mathur et al., 2008), the aforementioned genes are examples of genes encoding polypeptides that confer abiotic stress tolerance to plants.

In the present invention the inventors have shown that transformation of a dicot with the derivative promoter fragments of the invention results in the transcription of heterologous transcribable DNA sequence which is operably linked to and under the control of the promoter. It is however expected that as the derivative promoter fragments were isolated from a monocot plant, *Xerophyta viscosa* that they will perform as well, if not better, in a monocot plant.

The construct comprising a derivative promoter fragment of the invention and the heterologous transcribable DNA sequence of interest could be used to transform any plant which may be susceptible to abiotic stress, in particular crop plants, such as maize, wheat, rice, tabacco, cassava, sorghum, sweet potatoes barley, oats, rye, soybean, alfalfa, sunflower, cotton, canola and the like. Therefore, one possible commercial use of the derivative abiotic stress-inducible promoter fragments, is to generate physiologically normal plants despite being exposed to an abiotic stress. It may also be desirable to use the system to inducibly switch on other plant or foreign genes, such as bacterial, viral or fungal genes in a transgenic plant by subjecting the transgenic plant to abiotic stress.

The present invention is further described by the following examples. These examples, however, are not to be construed as limiting in any way either the spirit or scope of the invention.

Example 1

Mutagenesis of XvPSap1

Internal deletions were performed on the XvPSap1 (SEQ ID NO:9) promoter in the recombinant pBluescript::XvPSap1 plasmid to generate four shortened promoter fragments designated XvPSap1D (SEQ ID NO:1), XvPSap1E (SEQ ID NO:2), XvPSap1F (SEQ ID NO:7) and XvPSap1G (SEQ ID NO:3). Two forward primers (Primer A (SEQ ID NO:12) and Primer B (SEQ ID NO:13)) and two reverse primers (Primer C (SEQ ID NO:14) and Primer D (SEQ ID NO:15)) were designed (Table 1). Primers A and B bind to the 3'-end of XvPSap1 for amplification of 378 bp and 575 bp fragments of the XvPSap1 promoter, respectively (FIG. 10A). Similarly, primers C and D bind to the 5'-end of XvPSap1 for amplification of 546 bp and 358 bp fragments of the XvPSap1 promoter, respectively (FIG. 10A). The mutagenesis strategy involved the use of combinations of the respective forward and reverse primers to generate the four putative promoters in linearised pBluescript vector (FIG. 10B). Primer set B and C generated the XvPSap1D promoter fragment, B and D generated the XvPSap1E promoter fragment, A and C generated the XvPSap1F promoter fragment and A and D generated the XvPSap1G promoter fragment.

TABLE 1

Primers used to produce the respective pBluescript::XvPSap1 promoter fragments

| PRIMER NAME | SEQUENCE | SEQ ID NO: | TARGET | PRODUCT |
|---|---|---|---|---|
| Primer B | 5'-CAGATCTATCTTAGAATTGGACAGGGTG-3' | SEQ ID NO: 13 | XvPSap1 | pBluescript- |
| Primer C | 5'-AAGATCTCCATGGAAAGTGACGGAAC-3' | SEQ ID NO: 14 | XvPSap1 | XvPSap1D |
| Primer B | 5'-CAGATCTATCTTAGAATTGGACAGGGTG-3' | SEQ ID NO: 13 | XvPSap1 | pBluescript- |
| Primer D | 5'-AAGATCTAATGCACGTGAACTTTCTTAC-3' | SEQ ID NO: 15 | XvPSap1 | XvPSap1E |
| Primer A | 5'-CAGATCTACGTGGTGCATTTTCTAACAC-3' | SEQ ID NO: 12 | XvPSap1 | pBluescript- |
| Primer C | 5'-AAGATCTCCATGGAAAGTGACGGAAC-3' | SEQ ID NO: 14 | XvPSap1 | XvPSap1F |
| Primer A | 5'-CAGATCTACGTGGTGCATTTTCTAACAC-3' | SEQ ID NO: 12 | XvPSap1 | pBluescript- |
| Primer D | 5'-AAGATCTAATGCACGTGAACTTTCTTAC-3' | SEQ ID NO: 15 | XvPSap1 | XvPSap1G |

For each amplification, 25 µl reaction volumes were set up as follows: 1× standard buffer, 0.4 µM of each primer, 0.2 mM dNTP mixture, 0.04 U/µl Taq polymerase, 5 ng/ul template DNA made up to the final volume with dH$_2$O. A high fidelity polymerase (Phusion High-Fidelity DNA Polymerase, Thermo Scientific), which has proofreading activity was used. Amplification was carried out with the following conditions: 94° C. for 5 min; 5 cycles of 94° C. for 30 s, 52° C. for 45 s, 68° C. for 1 min; followed by 25 cycles of 94° C. for 30 s, 56° C. for 45 s, 68° C. for 1 min; and a final extension of 68° C. for 10 min. The PCR reaction was performed using a GeneAmp 9700 thermal cycler (Applied Biosystems).

The generated PCR products were electrophoresed on a 1% EtBr stained agarose gel. The bands of interest were excised and purified using the Wizard SV Gel Purification Kit (Promega) according to the manufacturer's instructions The linearised pBluescript DNA was treated with Klenow Fragment exo-(Fermentas), according to the manufacturer's instructions, to facilitate blunt end cloning. Standard blunt end ligation reactions of the linearised pBluescript DNA containing the XvPSap1D, E, F and G promoter fragments were set up as follows: linearised vector was religated in a total reaction volume of 20 µl, each ligation reaction contained 10 U of T4 DNA ligase and Ligase Buffer (New England Biolabs, USA) at a final concentration of 1×, the ligation reaction was mixed gently, briefly centrifuged and then incubated for 16 hours at 4° C.

The recombinant pBluescript plasmids (pBluescript:: XvPSap1D, E, F and G) were transformed into competent *E. coli* DH5α cells. Competent cells were allowed to thaw on ice. Thereafter, 10 µl of ligation mix was added to a 100 µl aliquot of competent cells and mixed gently. This transformation mix was incubated for 10 min on ice and then heat shocked by incubation for 5 min at 37° C. followed immediately by incubation for 2 min on ice. Eight hundred microliters of LB broth was added to the transformed cells and incubated for 1 h at 37° C. with vigorous shaking. One hundred microliters of the transformation mix was plated on LB agar plates supplemented with ampicillin (100 µg/ml) and incubated for 16 h at 37° C.

Colony PCR was performed to identify transformed clones using promoter specific primers (EcoRI-XvPsap1-F 5'-GGAATTCACTGTCTGGTAGCTGG-3' (SEQ ID NO: 16) and (BamHI-XvPSap1-R 5'-TCCGGATCCTC-CCTAATATCTCTCGCTC-3' (SEQ ID NO:17)). A 25 µl PCR amplification reaction was set up as follows: 1× standard buffer, 0.4 µM of each primer, 0.2 mM dNTP mixture, 0.04 U/µl Taq polymerase, 5 ng/ul template DNA made up to the final volume with dH$_2$O. A thermostable DNA polymerase, Supertherm Polymerase (Bertec Enterprise) was used for amplification. Amplification was carried out with the following conditions: 94° C. for 5 min; 30 cycles of 94° C. for 30 s, 59° C. for 45 s, 72° C. for 1 min; and a final extension of 72° C. for 10 min.

Colonies that were observed to be positive by colony PCR screening were inoculated into 5 ml LB broth supplemented with 100 µg/ml ampicillin and incubated for 16 h at 37° C. with shaking. For each construct, plasmid DNA from 3 different clones was isolated using the Bioflux Plasmid DNA Extraction and Purification Kit (Bioer) according to the manufacturer's instructions. The purified plasmid DNA was stored at −20° C. Plasmid DNA was sequenced and based on the sequence data, one recombinant plasmid for each promoter construct was selected for further downstream analysis.

Figure 11:
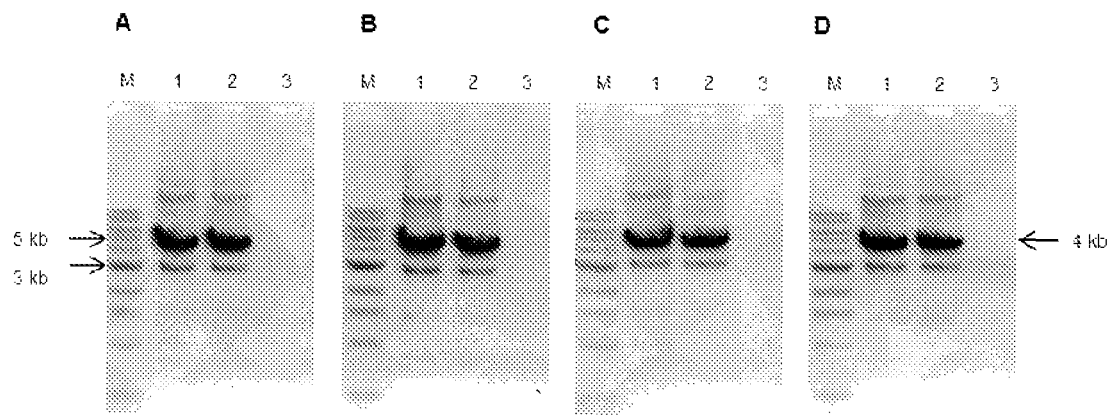
FIG. 11: shows amplification of pBluescript DNA incorporating the promoter fragments. A: pBluescript:: XvPSap1D. B: pBluescript::XvPSap1E. C: pBluescript::XvPSap1F. D: pBluescript::XvPSap1G. Lane M: 1 kb DNA ladder. Lane 1 and 2: pBluescript::promoter fragments. Lane 3: NTC.

The pBluescript::promoter fragments were successfully amplified, however non-specific amplification was also observed evidenced by the higher and lower molecular weight bands (FIG. 11). An intense band, corresponding to a fragment of approximately 4 kb, was observed in lanes 1 and 2. This band corresponds to the expected size of the linear pBluescript::XvPSap1D, E, F and G promoter fragments (FIGS. 11A, B, C and D, respectively). As a negative control, control PCR reaction without template was included. No amplification was observed in this control reaction.

The amplified DNA fragments were successfully excised, purified and treated with Klenow polymerase to facilitate blunt end ligation. Ligation mixtures were transformed into competent *E. coli* DH5α cells. Fifteen colonies each for pBluescript::XvPSap1D, E, F and G constructs were selected for screening. All of the selected colonies contained the desired promoter fragment. Three colonies for each promoter fragment were selected for further analysis. Sequencing results confirmed that the four shortened promoter fragments had been successfully ligated in pBluescript.

Example 2

Generation of pBluescript::Promoter Fragment::luc:: NosT

Figure 12:
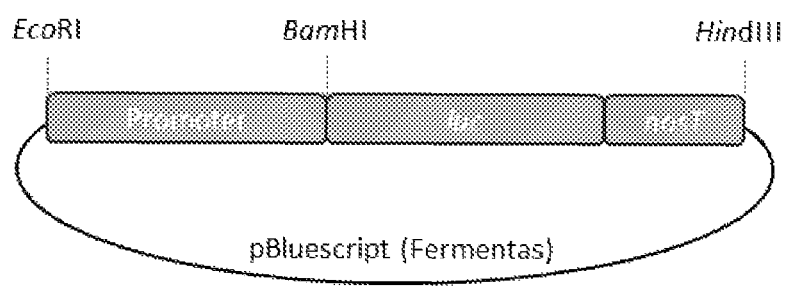
FIG. 12: shows a schematic illustration of the pBluescript promoter constructs.

Endonuclease digestion of the pBluescript vector containing the promoter fragments with EcoRI and BamHI allowed for cleavage of the promoter constructs from the pBluescript plasmid. Similarly, EcoRI and BamHI double digestion of pBluescript::XvPSap1::luc::NosT (FIG. 12) allowed for removal of the original XvPSap1 promoter, resulting in linearised pBluescript::luc::NosT with EcoRI and BamHI overhangs.

Three micrograms of each recombinant pBluescript plasmid was digested in a total volume of 60 µl using EcoRI and BamHI (FastDigest, Fermentas). The reaction mixture contained 6 µl of 10× FastDigest buffer, 3 units FastDigest EcoRI and 3 units FastDigest BamHI. Similarly, 4 µg of pBluescript::XvPSap1::luc::NosT was digested in a total volume of 80 µl using EcoRI and BamHI (FastDigest, Fermentas). The reaction mixture contained 8 µl of 10× FastDigest buffer, 4 units FastDigest EcoRI and 4 units FastDigest BamHI. The digestion mixtures were incubated for 1 h at 37° C.

Digested products were electrophoresed on a 1% EtBr stained agarose gel and the desired digestion products excised and purified using the Wizard SV Gel Purification Kit (Promega) according to the manufacturer's instructions.

Site specific cohesive end ligation reactions were set up as follows: purified DNA fragments (insert DNA) were ligated to linearised vector in a reaction volume of 20 µl. Each ligation reaction contained 10 U of T4 DNA ligase and Ligase Buffer (New England Biolabs, USA) at a final concentration of 1×. The ligation reaction was mixed gently, briefly centrifuged and then incubated for 16 hours at 4° C.

The recombinant pBluescript plasmids (pBluescript:: XvPSap1D, E, F, G::luc::NosT) were transformed into competent *E. coli* DH5α cells according to the protocol described in Example 1. The transformed cells were plated on LB agar supplemented with 100 µg/ml ampicillin and incubated for 16 h at 37° C.

Colony PCR was performed to identify positively transformed clones using promoter specific primers (EcoRI-XvPsap1-F (SEQ ID NO:16) and (BamHI-XvPSap1-R (SEQ ID NO:17)). For each amplification, 25 µl reaction volumes were set up as follows: 1× standard buffer, 0.4 µM of each primer, 0.2 mM dNTP mixture, 0.04 U/µl Taq polymerase, 5 ng/ul template DNA made up to the final volume with dH$_2$O. Amplification was carried out according to the protocol described in Example 1. Positive clones were inoculated into 5 ml LB broth supplemented with 100 µg/ml ampicillin and incubated for 16 h at 37° C. with shaking. For each recombinant plasmid, 3 different clones were isolated using the Bioflux Plasmid DNA extraction and Purification Kit (Bioer) according to the manufacturer's instructions.

Recombinant plasmid DNA was assessed by endonuclease digestion. Five hundred nanograms of recombinant plasmid DNA was digested in a total volume of 20 µl using EcoRI and BamHI (FastDigest, Fermentas). The reaction mixture contained 2 µl of 10× FastDigest buffer, 1 unit FastDigest EcoRI and 1 unit FastDigest BamHI. The reaction mixture was incubated for 1 h at 37° C. Thereafter, digested products were electrophoresed on a 1% EtBr stained agarose gel. One recombinant plasmid for each promoter construct was selected for further downstream analysis. Undigested plasmid DNA was stored at −20° C.

To facilitate later qualitative and quantitative analyses, the shortened promoters were individually cloned upstream of luc and NosT. To do this, the individual pBluescript vectors containing the shortened promoters, XvPSap1D, E, F and G were successfully digested with EcoRI and BamHI to release the respective promoter fragments. Single linear bands of 1.103 kb, 0.913 kb, 0.903 kb and 0.713 kb corresponding to the size of XvPSap1D, E, F and G, respectively, were observed following electrophoresis of the digestion products. Similarly, EcoRI and BamHI double digestion of pBluescript::XvPSap1::/luc::NosT was successful in removing the original XvPSap1 promoter, resulting in linearised pBluescript::luc::NosT with EcoRI and BamHI overhangs. A single band of approximately 5 kb, corresponding to the expected size of pBluescript::luc::NosT was observed when digestion products were electrophoresed.

The XvPSap1 promoter fragments of interest were successfully excised, purified and cohesive end ligation reactions were set up. Ligation mixtures were successfully transformed into competent E. coli DH5α cells.

Fifteen colonies for each construct were selected for screening. In each instance fourteen or fifteen colonies contained XvPSap1D, E, F or G.

Example 3

Generation of Binary Vector Constructs

Digestion of pBluescript::promoter_fragment::luc::NosT constructs with EcoRI and HindIII allowed for cleavage of each shortened promoter cassette from the recombinant plasmid. Similarly, the EcoRI and HindIII restriction double digestion of pTF101.1 (SEQ ID NO:29) resulted in linearised pTF101.1 with cohesive EcoRI and HindIII overhangs. pTF101.1 is a binary vector used in plant transformation protocols.

Initially, 3 µg of each recombinant plasmid was digested in a total volume of 20 µl using PvuII (Fermentas). The reaction mixture, containing 2 µl of 10× Buffer G and 1 unit PvuII, was incubated for 1 h at 37° C. The PvuII digest was necessary to differentiate between the promoter cassettes and the pBluescript vector due to their similar size (approximately 3 kb). PvuII cleaves pBluescript to yield two fragments of approximately 2.4 kb and a single 0.5 kb fragment. PvuII does not cleave the promoter constructs. Thus, it was possible to distinguish between pBluescript and the promoter cassettes. Digested products were electrophoresed on a 1% EtBr stained agarose gel and purified using the EZ-10 Spin Column PCR Purification Kit (Bio Basic Inc) according to the manufacturer's instructions.

The PvuII digested purified promoter cassettes were digested in a total volume of 50 µl using EcoRI and HindIII (FastDigest, Fermentas). The reaction mixture contained 5 µl of 10× FastDigest buffer, 3 units FastDigest EcoRI and 3 units FastDigest HindIII. The digestion mixtures were incubated for 1 h at 37° C. Similarly, 3 µg of pTF101.1 was digested using EcoRI and HindIII. Digested products were electrophoresed on a 1% EtBr stained agarose gel and the desired digestion products excised and purified using the Wizard SV Gel Purification Kit (Promega) according to the manufacturer's instructions.

Site specific cohesive end ligation reactions were set up as described in Example 2 for a vector to insert ratio of 1:3 using 50 ng of vector. Reaction components were mixed well and incubated for 16 h at 4° C.

Recombinant pTF101.1::promoter_fragment::luc::NosT was transformed into competent E. coli DH5α cells according to the protocol described in Example 1. The transformed cells were plated on LB agar supplemented with 100 µg/ml streptomycin and incubated for 16 h at 37° C.

Colony PCR was performed to identify positively transformed clones using promoter specific primers (EcoRI-XvPSap1-F (SEQ ID NO:16) and BamHI-XvPSap1-R (SEQ ID NO:17)). For each amplification, 25 µl reaction volumes were set up with component concentrations and colony PCR amplification conditions as described in Example 1.

Colonies observed to be positive by colony PCR screening were inoculated into 5 ml LB broth supplemented with 100 µg/ml streptomycin and incubated for 16 h at 37° C. with shaking. For each construct, plasmid DNA from 3 different clones was isolated using the Bioflux Plasmid DNA Extraction and Purification Kit (Bioer) according to the manufacturer's instructions.

The isolated recombinant plasmid DNA was assessed by endonuclease digestion. Five hundred nanograms of recombinant plasmid DNA was digested in a total volume of 20 µl using EcoRI and HindIII (FastDigest, Fermentas). The reaction mixture contained 2 µl of 10× FastDigest buffer, 1 unit FastDigest EcoRI and 1 unit FastDigest HindIII. The reaction mixtures were incubated for 1 h at 37° C. Thereafter, digested products were electrophoresed on a 1% EtBr stained agarose gel. One recombinant plasmid for each promoter construct was selected for further downstream analysis. Undigested plasmid DNA was stored at −20° C.

Figure 13:
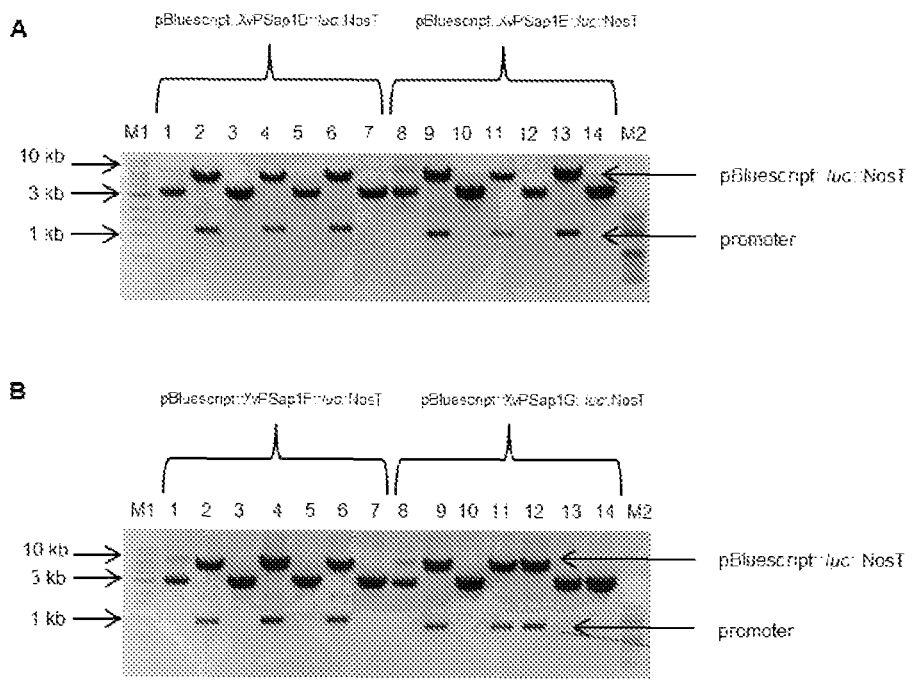
FIG. 13: shows a restriction endonuclease analysis of pBluescript::promoter::luc::NosT. A: pBluescript:: XvPSap1D::luc::NosT and pBluescript::XvPSap1E::luc:: NosT. Lane 1: Undigested pBluescript::XvPSap1D::luc:: NosT. Lanes 2, 4 and 6: EcoRI and BamHI restriction digests of pBluescript::XvPSap1D::luc::NosT. Lanes 3, 5 and 7: EcoRI and HindIII restriction digests of pBluescript:: XvPSap1D::luc::NosT. Lane 8: Undigested pBluescript:: XvPSap1E::luc::NosT. Lanes 9, 11 and 13: EcoRI and BamHI restriction digests of pBluescript::XvPSap1E::luc:: NosT. Lanes 10, 12 and 14: EcoRI and HindIII restriction digests of pBluescript::XvPSap1E::luc::NosT. B: pBluescript::XvPSap1F::luc::NosT and pBluescript::XvPSap1G:: luc::NosT. Lane 1: Undigested pBluescript::XvPSap1F:: luc::NosT. Lanes 2, 4 and 6: EcoRI and BamHI restriction digests of pBluescript::XvPSap1F::luc::NosT. Lanes 3, 5 and 7: EcoRI and HindIII restriction digests of pBluescript:: XvPSap1F::luc::NosT. Lane 8: Undigested pBluescript:: XvPSap1G::luc::NosT. Lanes 9, 11 and 12: EcoRI and BamHI restriction digests of pBluescript::XvPSap1G::luc:: NosT. Lanes 10, 13 and 14: EcoRI and HindIII restriction digests of pBluescript::XvPSap1G::luc::NosT. Lanes M1 and M2: 1 kb and 100 bp DNA ladder, respectively.

Three colonies for each of the promoter constructs were selected for plasmid isolation and restriction endonuclease analysis. Each isolated plasmid was subjected to EcoRI and HindIII digestion and thereafter electrophoresed. For all samples, a band of approximately 3 kb was observed (FIG. 13). This was expected as both the vector backbone and promoter::luc::NosT constructs are approximately 3 kb. An EcoRI and BamHI restriction endonuclease reaction was also performed to differentiate between the pBluescript vector and the promoter::luc::NosT cassettes. In this instance, two distinct DNA fragments corresponding to the promoter and the pBluescript::luc::NosT fragments were expected. Following digestion, two distinct bands were observed (FIG. 13). The larger approximately 5 kb fragment corresponded to the size of pBluescript::luc::NosT whereas the smaller fragments corresponded to the sizes of the various promoter fragments.

To facilitate plant transformation, the promoter::luc::NosT constructs were cloned into pTF101.1. The pTF101.1 vector is a binary vector containing the necessary DNA sequences for integration of transgenes into the plant genomic DNA. To differentiate between the pBluescript backbone and promoter_fragment::luc::NosT fragments generated by EcoRI and HindIII digestion, a PvuII digest of the four cloned constructs was successfully performed. The PvuII endonuclease cleaves pBluescript to yield two fragments of approximately 2.4 kb and 0.5 kb. It does not cleave the promoter cassettes of approximately 3 kb. The digestion products were purified and subjected to EcoRI and HindIII digestion. This allowed for cleavage of the promoter cassettes from pBluescript. Electrophoresis of the triple digested DNA revealed the presence of three fragments of the expected size. These were the 0.5 kb and 2.4 kb fragments corresponding to the digested pBluescript vector and a fragment of approximately 3 kb corresponding to the promoter cassettes. The EcoRI and HindIII double digestion of pTF101.1 was successful and resulted in linearised pTF101.1 with EcoRI and HindIII overhangs situated within the T-DNA region.

The DNA fragments corresponding to the pTF101.1 vector and promoter cassettes were successfully excised and purified. Specific cohesive end ligation reactions were set up and used to successfully transform competent E. coli DH5α cells.

Ten colonies for each construct were selected for screening. Six colonies contained XvPSap1D, nine contained XvPSap1E, eight contained XvPSap1F and seven contained XvPSap1G.

Figure 14:
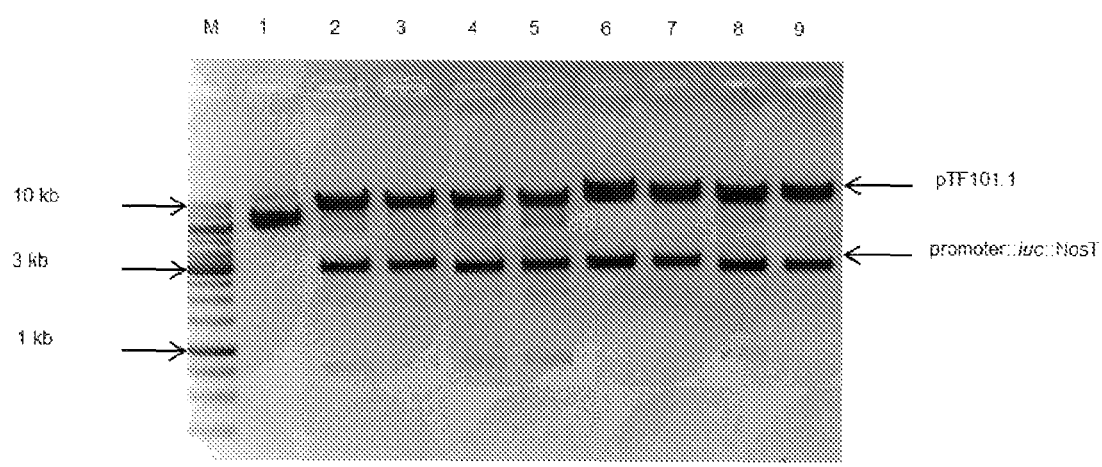
FIG. 14: shows EcoRI and HindIII restriction endonuclease digests of pTF101.1::promoter::luc::NosT plasmid DNA. Lane M: 1 kb DNA ladder. Lane 1: Undigested pTF101.1::promoter_fragment::luc::NosT DNA. Lane 2 and 3: Digested pTF101.1::XvPSap1D::luc::NosT. Lane 4 and 5: pTF101.1::XvPSap1E::luc::NosT. Lane 6 and 7: Digested pTF101.1::XvPSap1F::luc::NosT. Lane 8 and 9: Digested pTF101.1::XvPSap1G::luc::NosT.

Two colonies for each promoter were selected for plasmid isolation and EcoRI and HindIII restriction endonuclease analysis (FIG. 14). The digested pTF101.1::promoter_fragment::luc::NosT generated linear bands of approximately 3 kb and 9 kb for each construct. The smaller DNA fragment was the expected size for the promoter_fragment::luc::NosT cassette and the larger fragment corresponded to the size of the pTF101.1 vector. Both the PCR analysis as well as digestion results indicated that each promoter_fragment::luc::NosT cassette had been successfully cloned into the pTF101.1 binary vector.

Example 4

In Silico Analysis of Promoter Sequences

Following sequencing of the promoter fragments, the sequences were assessed for the presence of core and regulatory elements using the plantCARE software (Lescot et al., 2002).

In silico sequence analysis demonstrated that none of the promoter fragments used in this study displayed any significant sequence homology to any other known plant promoters except to XvPSap1. The shortened XvPSap1 promoters shared 82.57% sequence homology with each other.

The promoter core and cis-acting regulatory elements were predicted by the plantCARE bioinformatics tool. Four identical TATA-boxes were predicted in each promoter fragment within the 5'-300 bp region.

Various cis-acting elements were tentatively identified. These included elements involved in drought-, light- and low temperature-inducibility as well as in defense and biotic stress responsiveness. Cis-acting elements involved in abscisic acid, salicyclic acid and gibberellin responsiveness were observed. Additionally, elements involved in meristem expression, auxin-responsiveness and circadian control were also noted. Putative core and regulatory elements, including TC-rich repeats, MYB transcription factor binding site and ABA-response elements identified are indicated in FIG. 15.

Example 5

Transformation and Screening of Agrobacterium tumefaciens

The four pTF101.1 recombinant plasmids containing XvPSap1D::luc::NosT, XvPSap1E::luc::NosT, XvPSap1F::luc::NosT and XvPSap1G::luc::NosT were transformed into competent A. tumefaciens EHA101 cells. The transformation was carried according to the protocol described in Example 1 with two modifications. Firstly, transformed A. tumefaciens cells were incubated for 6 h at 30° C. instead of 1 hr at 37° C. Secondly, selection of transformed cells was performed on YEP agar supplemented with 100 μg/ml spectinomycin, 30 μg/ml chloramphenicol and 50 μg/ml kanamycin.

Colony PCR was performed to identify positively transformed clones using promoter specific primers (EcoRI-XvPSap1-F (SEQ ID NO:16) and BamHI-XvPSap1-R (SEQ ID NO:17)). For each amplification, 25 μl reaction volumes were set up as described in Example 1. Amplification was carried according to the protocol described in Example 1.

Colonies observed to be positive by colony PCR screening were inoculated into 10 ml YEP Broth supplemented with 100 μg/ml spectinomycin, 30 μg/ml chloramphenicol and 50 μg/ml kanamycin and incubated for 16 h at 30° C. with shaking. For each construct, plasmid DNA from 3 different clones was isolated using the Bioflux Plasmid DNA Extraction and Purification kit (Bioer) according to the manufacturer's instructions.

The isolated recombinant PTF101.1 plasmid DNA was verified to contain the entire promoter cassette by endonuclease digestions with EcoRI and HindIII. Digestion reactions were carried out according to the protocol described in Example 3. One recombinant plasmid for each promoter construct was selected for further downstream analysis. Glycerol stocks were synthesised by adding 200 μl of cells to 800 μl of autoclaved 50% glycerol, the mixture was gently mixed and stored at −80° C.

The pTF101.1 constructs were successfully transformed into competent Agrobacterium EHA101 cells. Fifteen colonies for each pTF101.1 construct were selected for screening and each contained the relevant promoter fragment. Five colonies for each of the pTF101::promoter_fragment::luc::NosT constructs were selected for further analysis. The presence of the pTF101.1 constructs in EHA101 was successfully verified by EcoRI and HindIII digestion.

Example 6

Agrobacterium-Mediated Transformation of Nicotiana tabacum with pTF101.1 Vector Constructs Fifty microliters of wild type N. tabacum (SR1 ecotype) seed was transferred to a sterile 2 ml Eppendorf. Seeds were sterilised in a solution containing 1 ml of 20% JIK supplemented with 0.1% Tween20, the mixture was briefly vortexed and incubated for 15 min at room temperature. The mixture was centrifuged for 30 s at 16000×g and the JIK solution removed. The sterilised seeds were washed in 1 ml sterile water, vortexed for 30 sec and centrifuged for 1 min at 16000×g. The water was removed and the washes repeated 4 times. The sterilised seeds were dried between sterile filter paper and collected in a sterile 1.5 ml Eppendorf tube. Sterilised seeds were subsequently germinated on sterile potting soil mix. Plants were cultured in the growth room with set conditions (24° C.; 16 h light, 8 h dark). Plants were maintained at these conditions for 2 to 3 months and watered twice weekly. Plants were treated with 1.14 g/l phostrogen every second week.

Single colonies of the transformed *A. tumefaciens* carrying the individual XvPSap1 promoter fragment expression cassettes were inoculated into 10 ml of YEP media supplemented with 100 µg/ml spectinomycin, 30 µg/ml chloramphenicol and 50 µg/ml kanamycin. The cultures were incubated for 16 h at 30° C. One ml of the 16 h culture was inoculated into 200 ml of YEP media supplemented with the appropriate antibiotics. The cultures were incubated at 30° C. until an absorbance reading of approximately 0.8 at 600 nm was obtained. The cultures were centrifuged for 20 min at 6000×g at 4° C. The supernatant was discarded and the bacterial pellets resuspended in 50 ml of liquid co-cultivation media comprising MS basal salts supplemented with B5 vitamin solution, 30 g/l sucrose, 0.1 mg/l α-naphthaleneacetic acid, 1 mg/l 6-benzylamino purine and 100 µM/l acetosyringone. The pH was adjusted to 5.4 with 1 M KOH.

Four to six inch leaves were selected from 2 month old plants. Leaves were soaked in sterile water for 30 min and sterilised according to the protocol described above. Sterile leaves were sliced into uniform segments of 5 mm avoiding the leaf margins and mid vein. Leaf explants were placed adaxial side up onto pre-culture media. Pre-culture was comprised of MS basal salts supplemented with B5 vitamin solution, 30 g/l sucrose, 0.1 mg/l α-naphthaleneacetic acid, 1 mg/l 6-benzylamino purine, 100 µM/l acetosyringone and 8 g/l plant agar. The pH was adjusted to 5.7 with 1 M KOH.

Leaf disks were infected for 30 min in the dark with the *Agrobacterium* inoculum containing the promoter cassettes in sterile petri dishes. The petri dishes were agitated once every 10 min. Thereafter, infected leaf disks were blot dried on sterile filter paper. Negative controls infected with *A. tumefaciens* containing pTF101.1 vector only were also included.

Each infected explant was transferred to co-cultivation medium and incubated for 3 days at 23° C. (18 h light, 6 h dark; light intensity of 140 µmol/m²/s). The adaxial part of the leaf was kept in contact with the medium. The co-cultivation media comprised MS basal salts supplemented with B5 vitamin solution, 30 g/l sucrose, 0.1 mg/l α-naphthaleneacetic acid, 1 mg/l 6-benzylamino purine and 100 µM/l acetosyringone. The pH was adjusted to 5.4.

Following the 3 day co-cultivation period, leaf discs were selected on shooting medium comprising MS basal salts supplemented with B5 vitamin solution, 30 g/l sucrose, 0.1 mg/l α-naphthaleneacetic acid, 1 mg/l 6-benzylamino purine, 10 µg/l nyastatin, 250 mg/l carbenicillin and 3 mg/l BASTA. Leaf explants were placed under an 18 h light regime with light intensity of 140 µmol/m²/s at 28° C. Putative transformants were subcultured fortnightly onto fresh media until sizable shoots were formed. BASTA resistant shoots were selected, excised and transferred to rooting media. The rooting media comprised half strength hormone free MS basal salts supplemented with 10 mg/l sucrose, 10 µg/l nyastatin, 250 mg/l carbenicillin and 3 mg/l BASTA.

Putative transformants with well-established root systems were transferred to pots containing sterile potting soil and cultured with set conditions according to the following conditions 24° C.; 16 h light, 8 h dark. The plants were covered with saran wrap for 8 days to assist acclimatisation and minimise dehydration. Once acclimatised, the putative transformants were transferred to 6 inch pots containing potting soil under normal growth conditions. Mature plants were self-pollinated and seed was harvested from mature dry pods. The transformation efficiency (TE) was calculated according to the formula:

TE=((no. of positive transformants)/(no. of explants transformed))×100.

Putative transgenic tobacco seed was sterilised according to the protocol described above and germinated on MS media supplemented with 8 g/l agar and 3 mg/ml BASTA. The pH was adjusted to 5.7 with 1 M KOH. Plants were cultured in the growth room with set conditions (24° C.; 16 h day, 8 h night). The surviving BASTA resistant plants with well-established root systems were transferred to trays containing 0.1 g/l Gaucho SW treated potting soil and covered with saran wrap for 1 week. Three weeks later, BASTA resistant transgenic plants were transferred to pots containing 0.1 g/l Gaucho SW treated potting soil. Plants were treated with 1.14 g/l phostrogen every second week.

Two month old wild type *N. tabacum* plants were used for *Agrobacterium*-mediated transformation. After three weeks on shooting media, transformed leaf disks displayed minimal or no necrosis and remained green in colour. The emergence of shoots was clearly visible. When untransformed leaf disks were transferred to shooting media supplemented with 3 mg/l BASTA, total necrosis was visible with the disks exhibiting a brown colour.

The putative XvPsap1D, F and G transformants did not reveal any unusual or abnormal phenotypic traits. In contrast, some of the putative XvPSap1E transformants displayed signs of dwarfism. The T0 seeds were collected for all plants. Overall, mature pods gave large amounts of seed. However, some XvPSap1G plants yielded pods that contained no seed. The observed absence in seed and dwarfism in the mentioned plants could be attributed to the random insertion of the promoter cassettes into the genome of the plants.

Wild type seedlings displayed complete necrosis and failed to survive on the BASTA supplemented MS media. After screening the remaining plants for the presence of the promoter, positively transformed plants were transferred to individual pots.

Example 7

Screening of Putative Transgenic Plants
Leaves were sampled from putative transgenic plants and were flash frozen in liquid nitrogen. Genomic DNA was extracted using the Dellaporta extraction protocol (Dellaporta et al., 1983) with minor modifications. Leaf tissue was ground in liquid nitrogen using a mortar and pestle. Roughly 100 µg of ground tissue was transferred to a sterile 2 ml Eppendorf tube containing 1.4 ml of Extraction buffer (100 mM Tris-Cl pH 8, 50 mM EDTA pH 8, 500 mM NaCl and 10 mM β-mercaptoethanol) and 0.1 ml of 20% SDS and incubated for 10 min at 65° C. Thereafter, 500 µl of 5 M potassium acetate was added and the samples shaken vigorously for 5 min followed by incubation for 20 min at 4° C. The samples were then centrifuged for 20 min at 16000×g. The supernatant was transferred to a sterile 2 ml Eppendorf tube containing 1 ml isopropanol and mixed by gentle inversion. The genomic DNA was precipitated for 24 h at −20° C. followed by centrifugation for 15 min at 16000×g. The supernatant was discarded and the pellets were air dried for 10 min. The pellets were resuspended in 70 µl of Resuspension buffer (50 mM Tris-Cl pH 8, 10 mM EDTA pH 8 and 0.6 mg/ml RNase A) at room temperature. To remove insoluble debris, the samples were centrifuged for 5 min at 16000×g and the supernatant transferred to a sterile 1.5 ml Eppendorf tube containing 7.5 μl of 3 M potassium acetate and 50 μl isopropanol. The samples were mixed well, incubated for 15 min at 4° C. and centrifuged for 2 min at 16000×g. The supernatant was discarded and the genomic DNA pellets were washed with 1 ml of 80% absolute ethanol. The mixture was centrifuged for 2 min at 16000×g and the supernatant removed. The genomic DNA pellet was redissolved in 100 μl TE (10 mM Tris-Cl, 1 mM EDTA). The quality of the extracted genomic DNA was assessed by electrophoresis on a 1% EtBr stained agarose gel.

The presence of the bar gene was determined by PCR amplification of a 421 bp DNA fragment using gene-specific primers (BarI (SEQ ID NO:18) and BarII (SEQ ID NO:19 (Table 2))). For each amplification, 50 μl reaction volumes were set up with component concentrations as follows: 1× standard buffer, 0.4 μM of each primer, 0.2 mM dNTP mixture, 0.04 U/μl Taq polymerase, 5 ng/ul template DNA made up to the final volume with $dH_2O$. Amplification was carried out with the following conditions: 94° C. for 5 min; 35 cycles of 94° C. for 30 s, 56° C. for 45 s, 72° C. for 1 min; and a final extension of 72° C. for 10 min. The PCR reaction was performed using a GeneAmp 9700 thermal cycler (Applied Biosystems). The generated amplimers were electrophoresed on a 1% EtBr stained agarose gel.

Similarly, the presence of the promoter and luc gene was determined by PCR amplification of a fragment of approximately 2 kb using a promoter-specific forward (EcoR1-XvPSap1-F (SEQ ID NO:16) and a luc-specific reverse (SEQ ID NO:20) primer pair (Table 2). For each amplification, 50 μl reaction volumes were set up with component concentrations as described above. Amplification was carried out with the following conditions: 94° C. for 5 min; 35 cycles of 94° C. for 30 s, 54° C. for 2 min, 68° C. for 90 s; and a final extension of 72° C. for 10 min.

TABLE 2

Primer sets used for screening of putatitive transgenic plants

| PRIMER NAME | SEQUENCE | SEQ ID NO: | TARGET |
|---|---|---|---|
| EcoR1-XvPSap1-F | 5'-GGAATTCACTGT CTGGTAGCTGG-3' | SEQ ID NO: 16 | XvPSap1 |
| BamHI-XvPSap1-R | 5'-TCCGGATCCTCCCT AATATCTCTCGCTC-3' | SEQ ID NO: 17 | XvPSap1 |
| BarI | 5'-GGTCTGCACC ATCGTCAACC-3' | SEQ ID NO: 18 | bar gene |
| BarII | 5'-GTCATGCCAG TTCCCGTGCT-3' | SEQ ID NO: 19 | bar gene |
| EcoRI-XvPSap1-F | 5'-GGAATTCACTG TCTGGTAGCTGG-3' | SEQ ID NO: 16 | XvPSap1 |
| luc-R3 | 5'-AGCAGCGCACT TTGAATCTT-3' | SEQ ID NO: 20 | luc gene |

For each genomic DNA isolation, an intense, high molecular weight band was visible, indicative of good, high quality DNA.

For plants harbouring the promoter cassettes, the presence of the promoter and luc gene was determined by amplification of a DNA fragment of approximately 3 kb using a promoter-specific forward and a luc-specific reverse primer. The *N. tabacum* plants transformed with the XvPSap1D, E, F and G constructs yielded two, one, zero and one transformation events, respectively. Since the transformation efficiency was relatively low, plants arising from a single transformation event were screened for the various promoter constructs. Twenty one *N. tabacum* plants transformed with the XvPSap1D construct were identified, seven with XvPSap1E, nine with XvPSap1G. No positive transformants were identified for XvPSap1F.

The transformation efficiency for each promoter construct was determined. An efficiency rate of 15%, 3.5% and 8% was calculated for XvPSap1D, E, G.

Example 8

Dehydration of Transgenic Plants

The dehydration treatments were carried out as described by Audran et al (1998) with the following modification: plants were dehydrated in soil instead of hydroponically. Six plants for each promoter fragment were used in the dehydration treatment. Prior to dehydration, plants were transferred to pots containing set amounts of soil and water. Plants were moved to Percival chambers (Percival Intellus control system) and incubated under set conditions (26° C.; 16 h day, 8 h night; 60% humidity; light intensity of 100 μmol/m²/s) for 1 week. Dehydration stress was carried out on whole plants and achieved by withholding water for 6 days. Throughout the dehydration period, four stressed tobacco leaves were sampled every 24 hours. The sampled leaves were used to assay for luciferase activity and immediately frozen in liquid nitrogen and stored at −70° C. The leaves were used for RNA isolations.

An additional twelve transgenic and six wild type plants were included in the dehydration stress treatment. Throughout the dehydration period, four leaves (representing a single plant) were sampled every 24 hours. The sampled leaves were used to estimate the relative water content.

The relative water content (RWC) was calculated for each sampled leaf or rosette at each time point. The fresh weight (FW) of each leaf was determined immediately after sampling. The full turgor weight (FTW) was determined after a 24 h immersion of the leaf in sterile water at room temperature. The leaves were then incubated for 48 h at 70° C. to determine the dry weight (DW). Relative water content was calculated according to the following formula:

RWC=((FW−DW)/(FTW−DW))×100.

The soil water content (SWC) of each pot containing a dehydrated plant was determined using the HH2 Moisture Meter (Delta-T Devices). Each pot was probed and the soil water content was determined in triplicate.

To determine whether the various promoters were functionally active in response to limited water conditions, transgenic plants were subjected to a six day dehydration treatment.

Morphological changes such as changes in leaf colour and textures were observed during the dehydration stress treatment. On days 0 and 1, the leaves were green and turgid for all plants. The leaves of treated plants began folding downward on days 2 to 3 and by day 4 to 5, they were completely folded and flaccid. In contrast, the leaves of the hydrated plants remained green and turgid throughout the six day period.

There were no notable differences in the morphological changes between the leaves of the transgenic and wild type plants. Both sets of plants appeared to display similar symptoms over the course of the treatment.

The four leaves selected for RWC determination were situated towards the middle of the plant. This was because the leaves situated closer to the apex of the plant were smaller, young leaves. While the leaves situated closer to the bottom of the plant were larger and older.

The RWC measurements obtained from both transgenic and wild type *N. tabacum* plants decreased from approximately 95% to 53%. The rate of dehydration for each plant was similar, as demonstrated by the RWC, during the treatment. However, on day 4 of the dehydration treatment, the transgenic plant had a lower RWC than the wild type plants. The RWC values of the hydrated transgenic plants fluctuated between 80% and 90% during the six day dehydration period.

The SWC was determined to see if the rate of water loss was similar across all pots and that the soil in certain pots was not drying significantly differently. The SWC in the pots containing plants undergoing dehydration stress treatment decreased on average from 33% to 5%. As with RWC measurements, a similar trend was observed between plants with respect to the soil drying. The SWC of the pots harbouring transgenic plants that were watered throughout the dehydration period fluctuated between 33% and 26%.

Example 9

Analysis of Promoter Activity by Live Imaging of Luciferase Expression

Prior to sampling for RNA isolations, leaves were individually sprayed and painted with equal amounts of 5 mM luciferin (VivoGlo, Promega). Luciferase activity was imaged with a 3D-luminometer consisting of a 0.5 square inch CCD camera and a field of view of 12.5 cm (Xenogen IVIS Lumina, Caliper) at an exposure time of 300 s per leaf. Photon or count emission by luciferase expressing leaves was quantified using the Living Image software (Caliper). The GFP assay was selected to negate any luminescence from chloroplasts.

The intact leaves of each plant were assayed for bioluminescence, due to luciferase activity, over a six day dehydration treatment. One plant for each promoter construct was assayed for bioluminescence per day. As expected, no bioluminescence was detected in the wild type plants as these do not contain the luciferase gene. The expression of luciferase was visible as bioluminescence in the leaves of T1 plants transformed with XvPsap1D, E and G. This was visible as blue (minimal activity), green (medium activity) and red (high activity) colouring within each leaf.

To quantify the levels of luciferase expression in each leaf, the region of interest (ROI) values were calculated. These values are a measure of the photons or counts that are detected due to the breakdown of luciferin to oxyluciferin. Overall, the number of counts increased over the dehydration period for plants transformed with XvPSap1D, E and G constructs (FIGS. 16B, C and D, respectively).

Figure 16:
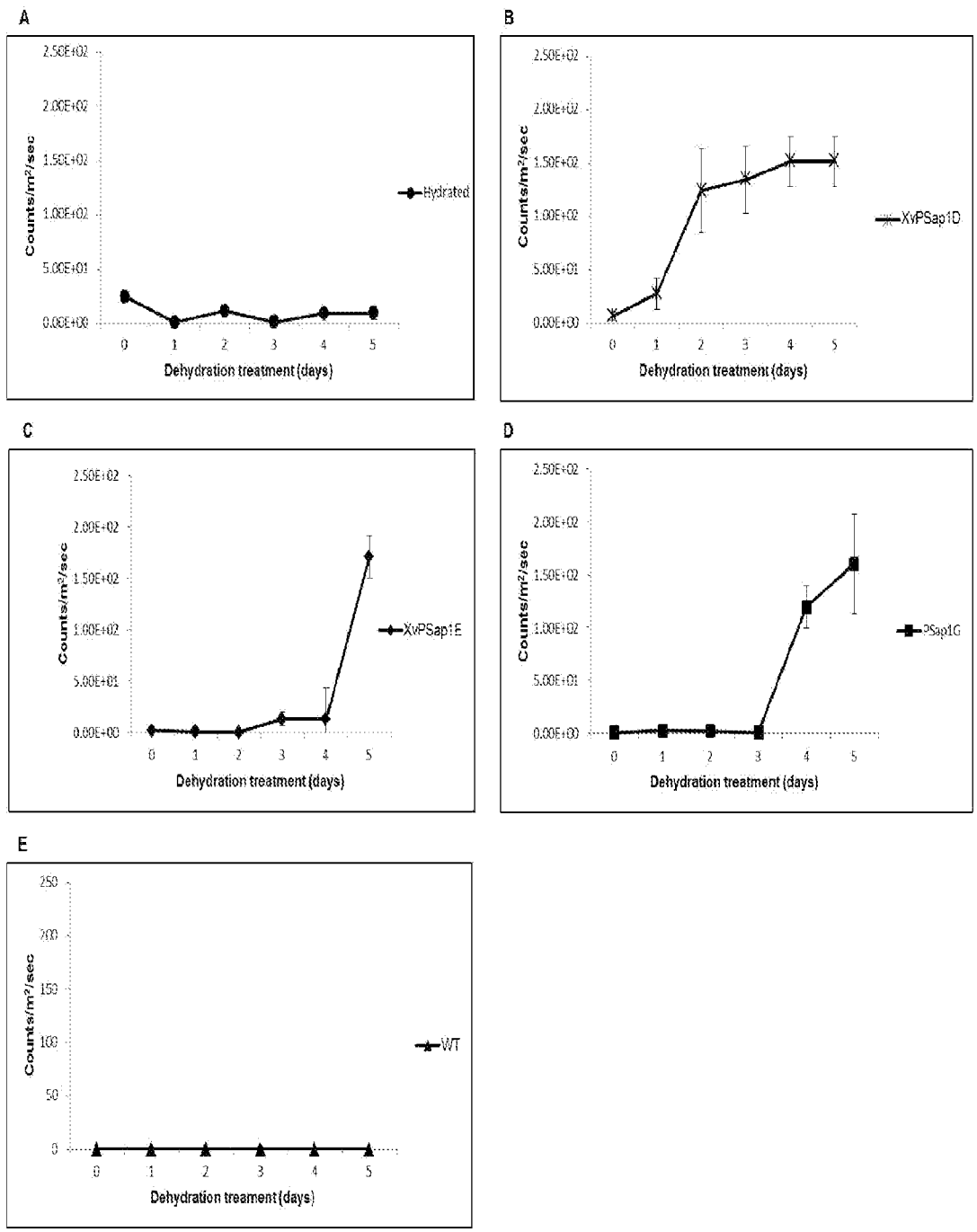
FIG. 16: shows luciferase activity in transgenic and wild type N. tabacum plants over a six day dehydration treatment. A: Hydrated transgenic plants. B: Transgenic plants transformed with XvPSap1D. C: Transgenic plants transformed with XvPSap1E. D: Transgenic plants transformed with XvPSap1G.

In plants that remained hydrated over the six day period, luciferase activity remained constant (FIG. 16A). In plants transformed with XvPSap1D, E and G, there were similar levels of activity over the course of the treatment (FIGS. 16B, C and D, respectively). For XvPSap1D, induction of activity began early (day 2) and was maintained over the rest of the dehydration period. For XvPSap1E and G, it began later (day 6 and 4, respectively). As expected, no induction was observed in wild type plants (FIG. 16E).

Example 10

Analysis of Luciferase Expression by Quantitative Real-Time PCR

All glassware and plastics used were double autoclaved and solutions were prepared with 0.001% diethylpyrocarbonate (DEPC) treated water. Each stored leaf was individually ground to a fine powder in liquid nitrogen with a mortar and pestle. The ground tissue was maintained at 4° C. during the extraction procedure to prevent RNA degradation. Approximately 600 mg of ground tissue was transferred to a sterile 2 ml Eppendorf tube containing 1 ml of One-Step reagent (Bio Basic) and mixed by inversion. Thereafter, samples were vortexed for 10 min at room temperature. To allow complete dissociation of the nucleoprotein complexes, the samples were incubated for 5 min at room temperature. Following incubation at room temperature, 200 µl of chloroform was added and the samples were inverted 30 times and then incubated for 3 min at room temperature. Samples were centrifuged for 15 min at 4° C. at 14000×g. The upper aqueous phase was carefully transferred to a fresh sterile 2 ml Eppendorf tube containing 1 ml of isopropanol and mixed by inversion. The mixture was allowed to settle for 10 min at room temperature before the RNA was pelleted by centrifugation for 15 min at 4° C. at 14000×g. The supernatant was discarded and the RNA pellet was washed with 1 ml of ice cold 75% ethanol, vortexed briefly and centrifuged for 10 min at 4° C. The supernatant was discarded and the RNA pellet was air dried for 5 min and dissolved in 89 µl of 0.01% DEPC treated water. Dissolution was enhanced by incubating the RNA for 10 min at 55° C. The RNA was stored at −70° C.

Each RNA extraction was treated with Deoxyribonuclease I (DNAse I; New England Biolabs) to digest and remove any genomic DNA contamination. The DNAse I reaction mixture consisted of 89 µl of isolated RNA, 10 µl of 10× DNAse buffer and 2 units of DNAse I in a total reaction volume of 100 µl. The reaction was mixed gently and incubated for 10 min at 37° C. The sample was purified using the GeneJet Plant RNA Miniprep Kit (Fermentas) according to the manufacturer's instructions. The purified RNA was quantified using the NanoDrop ND-1000 spectrophotometer (NanoDrop Technologies). The RNA integrity was assessed by electrophoresis at on a 1.2% EtBr stained agarose gel. Furthermore, the quality and integrity was assessed on a RNA-6000 Nano chip using the Agilent 2100 Bioanalyzer and analysed using the Agilent 2100 Expert Software (Anatech).

The concentration of RNA extracted for each isolation ranged from 89 to 543 ng/µl. Minimal to no degradation was observed when RNA was electrophoresed on a 1.2% non-denaturing agarose/EtBr gel. The 28S and 18S ribosomal RNA (rRNA) bands were clearly visible. Bands of lower molecular weight were also observed, corresponding to the 5S rRNA and chloroplast RNA.

The Agilent Expert software analyses RNA by assigning an RNA Integrity Number (RIN) to each sample. The RIN number is calculated based on the amount of signal found between the 5S and 18s rRNA and between the 18S and 28S rRNA bands. A RIN number of 10 indicates that the RNA is pure and that only 5S, 18S and 28S rRNA peaks are present. However, isolation of RNA from plant tissue also includes chloroplast RNA. This decreases the RIN value, but does not imply that the RNA is of poor quality. However purified RNA with a RIN number below 5.3 is generally considered to be of poor quality and not suitable for analysis.

The Agilent 2100 Expert Software generates an electropherogram with peaks corresponding to the different RNA species. The 5S, 18S and 28S rRNA bands are clearly visible as peaks. No genomic DNA contamination is present as that would be visible as a peak downstream of the 28S rRNA peak. The presence of chloroplast RNA is visible as peaks situated between the 5S and 18S rRNA. A post 28S rRNA hump is visible, corresponding to undenatured RNA.

The RNA extracted for each isolation was analysed using the Agilent 2100 Expert Software. The RIN values ranged from 4.6 to 8.8 and the concentrations from 100 ng/μl to 732 ng/μl. The electropherograms of RNA isolated from dehydration treated wild type and transgenic plants containing XvPSap1D, E, G as well as hydrated plants displayed all of the previously mentioned RNA species. RNA of either poor quality or low concentration was discarded.

The purified RNA extracted from the four leaf samples of each *N. tabacum* plants over the dehydration period were pooled and used for cDNA synthesis. Approximately 500 ng of RNA was used per cDNA synthesis reaction. This reaction was performed in quadruplicate to act as technical cDNA synthesis repeats. For cDNA synthesis, M-MuLV RNase H+ reverse transcriptase (Finnzymes) was used according to the manufacturer's instructions. The cDNA synthesis reaction mix consisted of approximately 500 ng of RNA, a final concentration of 0.05 μg oligo (dT)15 primers, 0.45 μg random hexamers, 1× RT buffer (includes dNTPs and MgCl2) and 0.04 μl M-MuLV RNase H+ reverse transcriptase (includes an RNA inhibitor) made up to a total volume of 20 μl with nuclease free water and mixed well. A ratio of 1:10 of random hexamers to oligo (dT)15 was selected for cDNA synthesis as this method increases the sensitivity of the synthesis reaction. The PCR cycle conditions consisted of incubation at 25° C. for 5 min, 42° C. for 1 hour, 85° C. for 15 min followed by a final step at 4° C. for 2 min. An aliquot of cDNA synthesis was electrophoresed on a 1.2% agarose/EtBr gel to analyse cDNA quality. The cDNA was stored at −20° C. until further use.

Serial dilutions of pooled cDNA from the treated samples were used to generate five-point standard curves. For the 18S rRNA and luciferase standard curves, a 10-fold and 3-fold dilution series was prepared respectively. For the L25 ribosomal protein and elongation factor-1α standard curves, a 4-fold dilution series was prepared.

Expression of the reference genes and luciferase gene was investigated by real time PCR using the Rotor Gene 6000 2 plex HRM (Corbett Life Science Research). The Kapa Sybr Fast Kit (Kapa BioSystems) master mix containing reaction buffer, heat activated DNA polymerase, dNTPs and a working concentration of 3 mM MgCl2 were used for each PCR reaction. Each PCR reaction contained a final concentration of 1× Kapa Sybr Fast, 0.04 μM gene specific primers (Table 3), 2 μl of cDNA and nuclease free water to a total volume of 20 μl. Gene specific primer sets for luciferase (RT-luc-F2 (SEQ ID NO:21) and RT-luc-R2 (SEQ ID NO:22), 18S rRNA (RT-18S-F3 (SEQ ID NO:23) and RT-18S-R3 (SEQ ID NO:24)), L25 ribosomal protein (RT-Rib-F3 (SEQ ID NO:25) and RT-Rib-R3 (SEQ ID NO:26)) and elongation factor1-α (RT-EF-F1 (SEQ ID NO:27) and RT-EF-R1 (SEQ ID NO:28)) were used in separate reactions. Each dilution point reaction was performed in quadruplicate. A no reverse transcription control (pooled RNA) as well as a no template control (NTC) was included in each real time run. Amplification was carried out with the following conditions: 95° C. for 5 min; 45 cycles of 95° C. for 5 s, 60° C. for 20 s, 72° C. for 5 s. Generation and analysis of standard curves were performed using the Rotor-Gene 6000 Series software (Corbett Life Science Research).

TABLE 3

Oligonucleotide primers for quantitative real time PCR

| PRIMER NAME | SEQUENCE | SEQ ID NO: | TARGET |
|---|---|---|---|
| RT-luc-F2 | 5'-ATCCAGAAGCCA CCAACGCCTTG-3' | SEQ ID NO: 21 | luc gene |
| RT-luc-R2 | 5'-CGAAGATGTTGGC GTGTTGGAGC-3' | SEQ ID NO: 22 | luc gene |
| RT-18S-F3 | 5'-GCAGCGGAAGTT TGAGGCAATAAC-3' | SEQ ID NO: 23 | 18S rRNA |
| RT-18S-R3 | 5'-CGACCTGATGA CTCGCGCTTAC-3' | SEQ ID NO: 24 | 18S rRNA |
| RT-Rib-F3 | 5'-GCAGATTCAGGAC AACAACACCCTTG-3' | SEQ ID NO: 25 | L25 ribosomal protein |
| RT-Rib-R3 | 5'-TTGTTGGCAACG TCCGAAGCATC-3' | SEQ ID NO: 26 | L25 ribosomal protein |
| RT-EF-F1 | 5'-GGTCACCAAGG CTGCTCAGAAG-3' | SEQ ID NO: 27 | Elongation factor 1-α |
| RT-EF-R1 | 5'-GCCTGTCAAC CACCCAGCTC-3' | SEQ ID NO: 28 | Elongation factor 1-α |

Real time PCR with the primer pairs for each reference gene was used to determine the expression stability of each of the potential reference genes. To minimise variations between PCR runs, all of the reactions containing one primer pair was performed in one run. The average expression levels were calculated from four technical repeats and by importing the relative standard curve into each run. Relative gene expression was determined by the amplification threshold in the exponential phase of the PCR, identifying the Ct value and comparing the Ct value to the standard curve (Muller et al., 2002). The stability of the potential reference genes were evaluated using both GeNorm and NormFinder (GenEx, MultiD).

Real time PCR reaction mixes and conditions were set up as above. To minimise variations between PCR runs, all of the reactions containing one primer pair was performed in one run. The standard curves were imported into each run to determine the Ct values and concentrations of the gene of interest and the reference gene. The determined values of the gene of interest were divided by that of the reference gene. The averages of the calculated values were used for relative quantification of the gene of interest. The value obtained for transcript levels on day 0 was used as a calibrator to determine whether a significant change in expression of the gene of interest occurs during dehydration. Relative quantification levels were determined using the GenEx software (MultiD) according to the Pfaffl equation (Pfaffl, 2001). The Pfaffl equation of one sample is the ratio of the gene of interest (target) versus a calibrator sample (control) and the reference gene (reference) versus a calibrator sample (control). The amplification efficiencies (E) were calculated according to the equation: $E=10^{[-1/slope]}$. The difference in Ct values of the target gene in the control and sample ($\Delta^{Ct}$ target) and in the reference gene in the control and sample ($\Delta^{Ct}$ reference) are considered (Pfaffl, 2001). The equation is as follows:

$$\text{Ratio} = ((E_{target})^{\Delta Ct\ target(control-sample)}) / ((E_{reference})^{\Delta Ct\ reference(control-sample)})$$

In order to quantify the luc gene expression levels, quantitative real time PCR was performed. This quantification was performed to confirm the results obtained from the promoter analysis in intact leaves.

The cDNA synthesis was successful as evidenced by a DNA smear following electrophoresis).

A single primer set was chosen for each amplimer based on analysis of product size and whether a single peak in the melt curve had been observed. A standard curve for each potential reference gene and luc gene was produced. The efficiencies, R-values and R^2-values for the potential reference genes are listed in Table 4.

TABLE 4

Efficiencies, R-values and R^2-values of the potential reference genes and luc gene.

| GENE | EFFICIENCY | R-VALUE | R^2-VALUE |
|---|---|---|---|
| 18S rRNA | 0.89 | 0.9991 | 0.9982 |
| EF-1α | 0.82 | 0.9994 | 0.9988 |
| L25 ribosomal protein | 0.79 | 0.9992 | 0.9984 |
| Luc | 0.99 | 0.9953 | 0.9905 |

Quantitative real-time PCR was performed on cDNA isolated from dehydration treated plants. The generated standard curve for each reference gene was imported and its stability of the reference gene was assessed using geNorm and NormFinder. geNorm is based on the assumption that the expression ratio between two genes should be the same if both are stably expressed (Vandesompele et al., 2001). The relative stability (M) of each gene is defined as the mean pairwise variation of the gene with the other reference genes. The lower the M value, the more stable the reference gene. geNorm identified both L25 ribosomal protein and EF-1α with an M value of 0.037785 as being the best reference genes.

NormFinder assesses the stability of the reference genes by comparing the variation between the genes. The reference genes that are most stable are those with the lowest variation. Normfinder identified EF-1α as the most stable reference gene followed by L25 ribosomal protein. Both programmes identified 18S rRNA as the least stable of the three.

Based on both geNorm and NormFinder analysis, EF-1α and L25 ribosomal protein were chosen as reference genes. It should be noted that Schmidt and Delaney (2010) also concluded that these genes were the most suitable in a *N. tabacum* dehydration stress treatment analysis.

The acquisition and purification of RNA is the first step in quantitative real time PCR and therefore RNA needs to be of high quality. Furthermore, the RNA should be free of genomic DNA, particularly if the target is a gene that lacks introns. Since the target gene (luc) does not contain any introns, an RNA control reaction was included in every real time run to demonstrate the absence of genomic DNA and subsequently confirm that any detected luc mRNA was not a product of genomic DNA contamination but rather of the cDNA template. In all of the real time runs, no luc mRNA was detected as a product of genomic DNA. The same result was obtained for the reference gene. No products were detected in the no template control reactions as well.

As with the analysis of luciferase activity in intact leaves, promoter analysis was determined in only one plant by measuring luc mRNA transcripts at each time point. A consequence is that a full analysis of the data was not possible. However, qRT-PCR was used as a tool to assess the promoter activity in T1 plants and not to determine absolute activity. The overall trend of each promoter thus was assessed. As no repeats were included in the study, standard deviation between readings was determined across leaves in a single plant.

Figure 17:
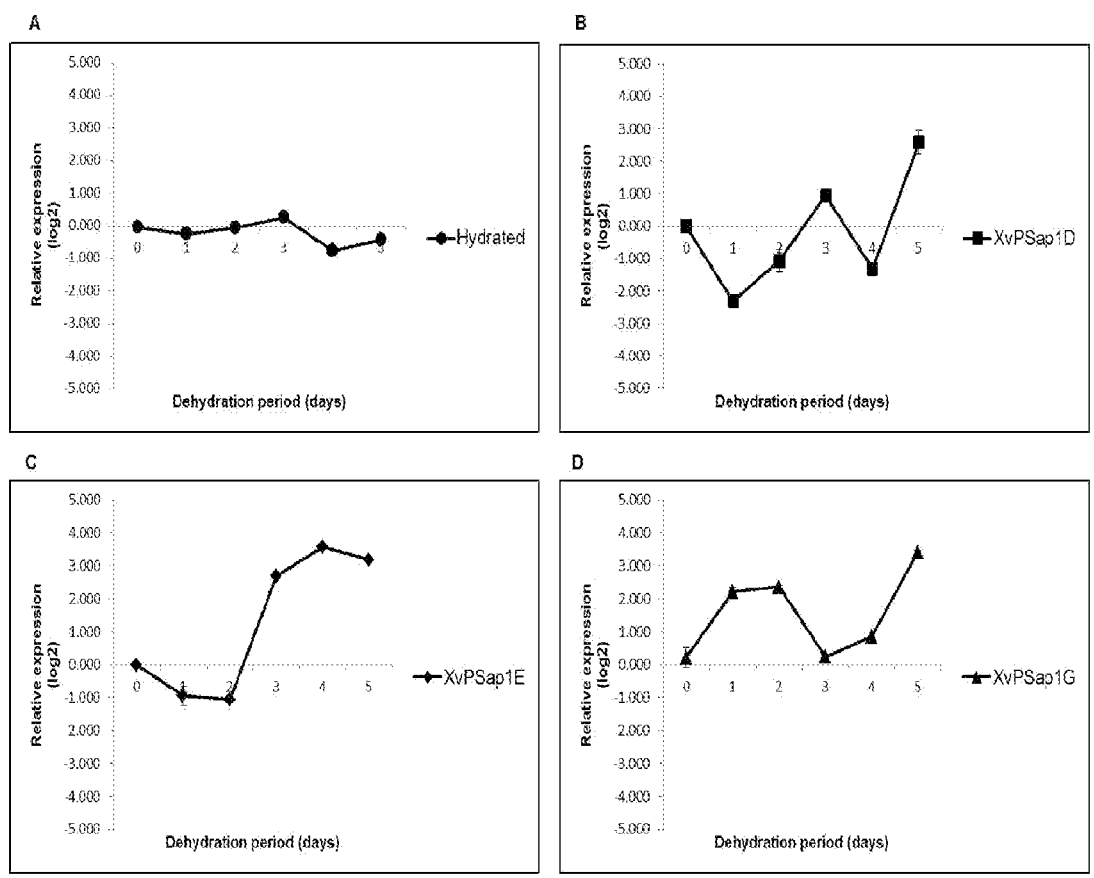
FIG. 17: shows luciferase mRNA levels in transgenic N. tabacum plants over six day dehydration treatment. A: Hydrated transgenic plants. B: Transgenic plants transformed with XvPSap1D. C: Transgenic plants transformed with XvPSap1E. D: Transgenic plants transformed with XvPSap1G.

Overall, the luc mRNA transcripts increased over the dehydration period for plants transformed with XvPSap1D, E and G and all of resulted in similar levels of induction (FIGS. 17B, C and D, respectively). In plants that remained hydrated over the six day period, the luc mRNA transcripts remained constant (FIG. 17A). For XvPSap1E, induction began early (day 2 and 3) and was maintained over the rest of the dehydration period. For XvPSap1D and G, induction also began early (day 1) but transcript levels decreased on day 3 and 2, respectively, before increasing again towards the end of the dehydration period. As expected, no induction was observed in wild type plants.

Although analysis was only determined in one biological plant at each time point, an overall trend was clearly observed. All of the promoter fragments were able to drive expression of the luc mRNA transcripts. Over the dehydration period, the levels of those transcripts increased to a similar level.

Example 11

To verify the promoter expression results obtained in T1 transgenic plants the methodologies used in Examples 9 and 10 were repeated with minor modifications as described below. T3 transgenic plants transformed with either the XvPSap1D or XvPSap1G derivative promoter constructs were used. In this example, four biological plants were used per derivative promoter construct. For each of the biologicals five technical repeats were included.

Dehydration treatments were carried out as described in Example 8 of the specification with the following minor modifications. For each treatment, 24 plants for each promoter fragment (XvPSap1D and XvPSap1G) were exposed to dehydration treatment for analysis of promoter activity. Additionally, 24 plants (XvPSap1D) were included in the dehydration treatment for determination of relative water content (RWC).

Figure 18:
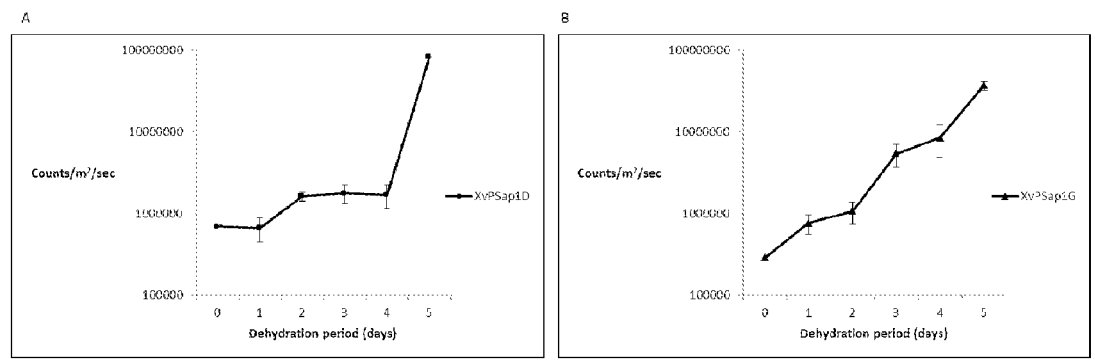
FIG. 18: shows luciferase activity in transgenic N. tabacum plants over a six day dehydration treatment. A: T3 transgenic plants transformed with XvPSap1D. B: T3 transgenic plants transformed with XvPSap1G. Each data point represents the mean and standard deviation of four biological plants.

Further, live imaging of luciferase expression was carried out as described in Example 9 with the following modifications. T3 transgenic plants transformed with either the XvPSap1D or XvPSap1G derivative promoter constructs were used. Further, four biological plants were used per promoter construct as compared to one in Example 9. Accordingly, in FIG. 18 a single data point is reflective of data obtained from the mean of expression results accumulated from a total of 16 leaves.

Figure 19:
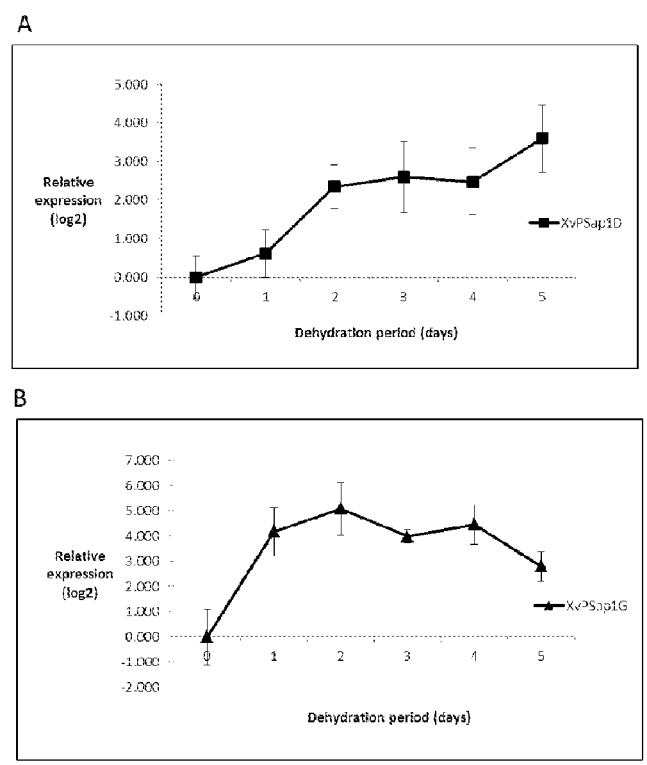
FIG. 19: shows luciferase mRNA levels in transgenic N. tabacum plants over six day dehydration treatment. Data points represent the mean of 20 repeats (4 biologicals with 5 technicals each). A: T3 transgenic plants transformed with XvPSap1D. B: T3 transgenic plants transformed with XvPSap1G. Error bars represent the standard deviation of five technical repeats for four biological plants at each time point.

Similarly, an analysis of luciferase expression by quantitative real-time PCR was performed as described in Example 10 using T3 transgenic plants. Four biological plants were used per promoter construct and five technical repeats were performed per plant. The results of this analysis are shown in FIG. 19.

REFERENCES

Audran, C., et al. (1998) *Plant Physiology*, 118:1021-1028.
Bhatnagar-Mathu, P., et al. (2008) *Plant Cell Rep*, 27:411-424.
Dellaporta, S. L., et al. (1983) *Plant Molecular Biology*, 1: 9-21.
Garwe, D., et al. (2006) *Biotechnology Journal*, 1(10):1137-1146.
Garwe, D., et al. (2003) *Experimental Botany*, 54:191-201

Iyer, R., et al. (2007) In Plant Desiccation Tolerance. Edited by Jenks M. A. and Woods A. J. Blackwell Publishing Ltd, Oxford, UK, pp 283-296.

Lescot M., et al. (2002) *Nucleic Acids Research*, 30(1):325-327.

Muller, P. Y., et al. (2002) *Biotechniques*, 32:1372-1379.

Oduor, R. O. (2009) PhD Thesis. Department of Molecular and Cell Biology, University of Cape Town, South Africa.

Schmidt G. W. and Delaney S. K. (2010) *Molecular Genetics and Genomics*, 283:233-241.

Vandesompele, J., et al. (2002) *Genome Biology*, 3:Research0034.

Woo, N. S., et al. (2008) *Plant Methods*, 4:27.

---

The invention claimed is:

1. A promoter comprising the nucleic acid sequence of any one of SEQ ID NOs: 1-3.

2. An expression cassette comprising the promoter of claim 1 operably linked to a heterologous transcribable DNA sequence and, optionally, a terminator sequence operably linked to the heterologous transcribable DNA sequence.

3. A recombinant vector comprising the expression cassette of claim 2.

4. A host cell transformed with the recombinant vector of claim 3.

5. A transgenic plant comprising the host cell of claim 4.

6. A transgenic seed obtained from the transgenic plant of claim 5, wherein said seed comprises said recombinant vector.

7. A method of regulating the transcription of a heterologous transcribable DNA sequence in a host cell, the method comprising transforming the host cell with the nucleotide cassette of claim 2.

8. A method of regulating the transcription of a heterologous transcribable DNA sequence in a transgenic plant, the method comprising stably transforming the plant with the nucleotide cassette of claim 2.

9. A method of producing a transgenic plant, the method comprising introducing the nucleotide cassette of claim 2 into a plant cell, and regenerating a transgenic plant from the plant cell.

10. The transgenic plant of claim 5, wherein the transgenic plant is a monocotyledonous or dicotyledonous plant.

11. The transgenic plant of claim 5, wherein the transgenic plant is selected from the group consisting of maize, rice, sorghum, wheat, cassava, barley, oat, rye, sweet potato, soybean, alfalfa, tobacco, sunflower, cotton, and canola.

12. The transgenic plant of claim 11, wherein the transgenic plant is a tobacco plant.

13. The method of claim 8, wherein the transgenic plant is a monocotyledonous or dicotyledonous plant.

14. The method of claim 8, wherein the transgenic plant is selected from the group consisting of maize, rice, sorghum, wheat, cassava, barley, oat, rye, sweet potato, soybean, alfalfa, tobacco, sunflower, cotton, and canola.

15. The method of claim 14, wherein the transgenic plant is a tobacco plant.

16. The method of claim 9, wherein the transgenic plant is a monocotyledonous or dicotyledonous plant.

17. The method of claim 9, wherein the transgenic plant is selected from the group consisting of maize, rice, sorghum, wheat, cassava, barley, oat, rye, sweet potato, soybean, alfalfa, tobacco, sunflower, cotton, and canola.

* * * * *

SEQUENCE LISTING

```
<160> NUMBER OF SEQ ID NOS: 36

<210> SEQ ID NO 1
<211> LENGTH: 1120
<212> TYPE: DNA
<213> ORGANISM: Artificial Sequence
<220> FEATURE:
<223> OTHER INFORMATION: XvPSap1D promoter fragment

<400> SEQUENCE: 1
actgtctggg tagctggcaa tatagagacg taaataattg tctgtaaata gggagaaatt       60
catggatcat caccctaatt cggtctttca ctcattttat catagacctg actaaagaac      120
ttggtcagag ttttttactta tttaaaataa agaggacttc atggcatcca tgtgcaggta     180
cagctcccag aaaaaaaagc atgaaacacg agaggatcaa tagcattcga tctgaaacaa     240
aaggttgcag ctcaagactt tctccaaaat attaagatga tccaaagaat taccccaaga     300
tatccaacgt ataccaatgt gtataccgaa agtaagaaag ttcacgtgca ttctttgatt     360
tttctcccga gtgttctttt ctgaaatgag taaataagac tagaataaga gctaatgtat     420 ttttttttcta aaaaagttg aatgtggata caatatgatt atacattcat tagctatttt    480
aagtatattc tattttttt cccccaaaa gaacacaaat gtgttccgtc actttccatg      540
gagatcagat ctatcttaga attggacagg gtgcttatga tacaacttgt tcctatcaac     600
aactgcatgt tagacagcgc cgaatttaca gtcctactgg gcgccacttt tcaacccaca     660
tcatcaagat gaacaccacg ttatcttcat ccgctccaac cacatggtcc agcgccactg     720
gccaagaccg ccagccagcc aggccatcca acgtggtgca ttttctaaca ctccacgttc     780
gctgtacggc attatttctc cagccagaaa gaccgagaca gcgacgctgt tgggcgggcc     840
cgcggcctgc tctctctgct tccccatgag attcacgggc atcgctcctc gctcgtgcct     900
acgcgaccgc gccgatccac gtgacgtggc gcagcaatcg ttcttactag gcgcttgcac     960
gtgtcgttcg catgcgaagc gtccacactg ccaacgacct ccttaaatat ccttgtgata    1020
ttcgccttac gatctcacac ttcgcacgca aaggccagtc gcagatttgg gttgaatttg    1080
ctgcgttttg gcagattttg agcgagagat attagggaag                          1120

<210> SEQ ID NO 2
<211> LENGTH: 933
<212> TYPE: DNA
<213> ORGANISM: Artificial Sequence
<220> FEATURE:
<223> OTHER INFORMATION: XvPSap1E promoter fragment

<400> SEQUENCE: 2
actgtctggg tagctggcaa tatagagacg taaataattg tctgtaaata gggagaaatt       60
catggatcat caccctaatt cggtctttca ctcattttat catagacctg actaaagaac      120
ttggtcagag ttttttactta tttaaaataa agaggacttc atggcatcca tgtgcaggta     180
cagctcccag aaaaaaaagc atgaaacacg agaggatcaa tagcattcga tctgaaacaa     240
aaggttgcag ctcaagactt tctccaaaat attaagatga tccaaagaat taccccaaga     300
```

| tatccaacgt ataccaatgt gtataccgaa agtaagaaag ttcacgtgca ttagatctca | 360 |
| gatctatctt agaattggac agggtgctta tgatacaact tgttcctatc aacaactgca | 420 |
| tgttagacag cgccgaattt acagtcctac tgggcgccac ttttcaaccc acatcatcaa | 480 |
| gatgaacacc acgttatctt catccgctcc aaccacatgg tccagcgcca ctggccaaga | 540 |
| ccgccagcca gccaggccat ccaacgtggt gcattttcta acactccacg ttcgctgtac | 600 |
| ggcattattt ctccagccag aaagaccgag acagcgacgc tgttgggcgg gcccgcggcc | 660 |
| tgctctctct gcttccccat gagattcacg ggcatcgctc ctcgctcgtg cctacgcgac | 720 |
| cgcgccgatc cacgtgacgt ggcgcagcaa tcgttcttac taggcgcttg cacgtgtcgt | 780 |
| tcgcatgcga agcgtccaca ctgccaacga cctccttaaa tatccttgtg atattcgcct | 840 |
| tacgatctca cacttcgcac gcaaaggcca gtcgcagatt tgggttgaat tgctgcgtt | 900 |
| ttggcagatt ttgagcgaga gatattaggg aag | 933 |

<210> SEQ ID NO 3
<211> LENGTH: 732
<212> TYPE: DNA
<213> ORGANISM: Artificial Sequence
<220> FEATURE:
<223> OTHER INFORMATION: XvPSap1G promoter fragment

<400> SEQUENCE: 3

| actgtctggg tagctggcaa tatagagacg taaataattg tctgtaaata gggagaaatt | 60 |
| catggatcat caccctaatt cggtctttca ctcattttat catagacctg actaaagaac | 120 |
| ttggtcagag ttttttactta tttaaaataa agaggacttc atggcatcca tgtgcaggta | 180 |
| cagctcccag aaaaaaaagc atgaaacacg agaggatcaa tagcattcga tctgaaacaa | 240 |
| aaggttgcag ctcaagactt tctccaaaat attaagatga tccaaagaat taccccaaga | 300 |
| tatccaacgt ataccaatgt gtataccgaa agtaagaaag ttcacgtgca ttagacagat | 360 |
| ctacgtggtg cattttctaa cactccacgt tcgctgtacg gcattatttc tccagccaga | 420 |
| aagaccgaga cagcgacgct gttgggcggg cccgcggcct gctctctctg cttccccatg | 480 |
| agattcacgg gcatcgctcc tcgctcgtgc ctacgcgacc gcgccgatcc acgtgacgtg | 540 |
| gcgcagcaat cgttcttact aggcgcttgc acgtgtcgtt cgcatgcgaa gcgtccacac | 600 |
| tgccaacgac ctccttaaat atccttgtga tattcgcctt acgatctcac acttcgcacg | 660 |
| caaaggccag tcgcagattt gggttgaatt gctgcgtttt ggcagatttt gagcgagag | 720 |
| atattaggga ag | 732 |

<210> SEQ ID NO 4
<211> LENGTH: 1120
<212> TYPE: DNA
<213> ORGANISM: Artificial Sequence
<220> FEATURE:
<223> OTHER INFORMATION: Reverse complement XvPSap1D

<400> SEQUENCE: 4

| cttccctaat atctctcgct caaaatctgc caaaacgcag caaattcaac ccaaatctgc | 60 |
| gactggcctt tgcgtgcgaa gtgtgagatc gtaaggcgaa tatcacaagg atatttaagg | 120 |
| aggtcgttgg cagtgtggac gcttcgcatg cgaacgacac gtgcaagcgc ctagtaagaa | 180 |
| cgattgctgc gccacgtcac gtggatcggc gcggtcgcgt aggcacgagc gaggagcgat | 240 |
| gcccgtgaat ctcatgggga agcagagaga gcaggccgcg ggcccgccca acagcgtcgc | 300 |
| tgtctcggtc tttctggctg gagaaataat gccgtacagc gaacgtggag tgttagaaaa | 360 |

```
tgcaccacgt tggatggcct ggctggctgg cggtcttggc cagtggcgct ggaccatgtg    420
gttggagcgg atgaagataa cgtggtgttc atcttgatga tgtgggttga aaagtggcgc    480
ccagtaggac tgtaaattcg gcgctgtcta acatgcagtt gttgatagga acaagttgta    540
tcataagcac cctgtccaat tctaagatag atctgatctc catggaaagt gacggaacac    600
atttgtgttc ttttgggggg aaaaaaaata gaatatactt aaaatagcta atgaatgtat    660
aatcatattg tatccacatt caactttttt tagaaaaaaa atacattagc tcttattcta    720
gtcttattta ctcatttcag aaaagaacac tcgggagaaa atcaaagaa tgcacgtgaa     780 ctttcttact ttcggtatac acattggtat acgttgata tcttgggta attctttgga     840 tcatcttaat attttggaga aagtcttgag ctgcaacctt tgtttcaga tcgaatgcta     900 ttgatcctct cgtgtttcat gcttttttt ctgggagctg tacctgcaca tggatgccat     960
gaagtcctct ttatttaaa taagtaaaaa ctctgaccaa gttctttagt caggtctatg    1020
ataaaatgag tgaaagaccg aattagggtg atgatccatg aatttctccc tatttacaga   1080
caattattta cgtctctata ttgccagcta cccagacagt                         1120
```

<210> SEQ ID NO 5
<211> LENGTH: 933
<212> TYPE: DNA
<213> ORGANISM: Artificial Sequence
<220> FEATURE:
<223> OTHER INFORMATION: Reverse complement XvPSap1E

<400> SEQUENCE: 5

```
cttccctaat atctctcgct caaaatctgc caaaacgcag caaattcaac ccaaatctgc     60
gactggcctt tgcgtgcgaa gtgtgagatc gtaaggcgaa tatcacaagg atatttaagg    120
aggtcgttgg cagtgtggac gcttcgcatg cgaacgacac gtgcaagcgc ctagtaagaa    180
cgattgctgc gccacgtcac gtggatcggc gcggtcgcgt aggcacgagc gaggagcgat    240
gcccgtgaat ctcatgggga agcagagaga gcaggccgcg ggcccgccca acagcgtcgc    300
tgtctcggtc tttctggctg agaaataat gccgtacagc gaacgtggag tgttagaaaa    360
tgcaccacgt tggatggcct ggctggctgg cggtcttggc cagtggcgct ggaccatgtg    420
gttggagcgg atgaagataa cgtggtgttc atcttgatga tgtgggttga aaagtggcgc    480
ccagtaggac tgtaaattcg gcgctgtcta acatgcagtt gttgatagga acaagttgta    540
tcataagcac cctgtccaat tctaagatag atctgagatc taatgcacgt gaactttctt    600
actttcggta tacacattgg tatacgttgg atatcttggg gtaattcttt ggatcatctt    660
aatattttgg agaaagtctt gagctgcaac cttttgtttc agatcgaatg ctattgatcc    720
tctcgtgttt catgcttttt tttctgggag ctgtacctgc acatggatgc catgaagtcc    780
tctttatttt aaataagtaa aaactctgac caagttcttt agtcaggtct atgataaaat    840
gagtgaaaga ccgaattagg gtgatgatcc atgaatttct ccctatttac agacaattat    900
ttacgtctct atattgccag ctacccagac agt                                933
```

<210> SEQ ID NO 6
<211> LENGTH: 732
<212> TYPE: DNA
<213> ORGANISM: Artificial Sequence
<220> FEATURE:
<223> OTHER INFORMATION: Reverse complement XvPSap1G

<400> SEQUENCE: 6

```
cttccctaat atctctcgct caaaatctgc caaaacgcag caaattcaac ccaaatctgc        60
gactggcctt tgcgtgcgaa gtgtgagatc gtaaggcgaa tatcacaagg atatttaagg       120
aggtcgttgg cagtgtggac gcttcgcatg cgaacgacac gtgcaagcgc ctagtaagaa       180
cgattgctgc gccacgtcac gtggatcggc gcggtcgcgt aggcacgagc gaggagcgat       240
gcccgtgaat ctcatgggga agcagagaga gcaggccgcg ggcccgccca acagcgtcgc       300
tgtctcggtc tttctggctg agaaataat gccgtacagc gaacgtggag tgttagaaaa        360
tgcaccacgt agatctgtct aatgcacgtg aactttctta ctttcggtat acacattggt       420
atacgttgga tatcttgggg taattctttg gatcatctta atattttgga gaaagtcttg       480
agctgcaacc ttttgtttca gatcgaatgc tattgatcct ctcgtgtttc atgctttttt       540
ttctgggagc tgtacctgca catggatgcc atgaagtcct ctttatttta aataagtaaa       600
aactctgacc aagttcttta gtcaggtcta tgataaaatg agtgaaagac cgaattaggg       660
tgatgatcca tgaatttctc cctatttaca gacaattatt tacgtctcta tattgccagc       720
tacccagaca gt                                                          732

<210> SEQ ID NO 7
<211> LENGTH: 924
<212> TYPE: DNA
<213> ORGANISM: Artificial Sequence
<220> FEATURE:
<223> OTHER INFORMATION: XvPSap1F promoter fragment

<400> SEQUENCE: 7
actgtctggg tagctggcaa tatagagacg taaataattg tctgtaaata gggagaaatt        60
catggatcat caccctaatt cggtctttca ctcattttat catagacctg actaaagaac       120
ttggtcagag ttttactta tttaaaataa agaggactc atggcatcca tgtgcaggta        180
cagctcccag aaaaaaaagc atgaaacacg agaggatcaa tagcattcga tctgaaacaa       240
aaggttgcac ctcaagactt tctccaaaat attaagatga tccaaagaat taccccaaga      300
tatccaacgt ataccaatgt gtataccgaa agtaagaaag ttcacgtgca ttctttgatt       360
tttctcccga gtgttctttt ctgaaatgag taaataagac tagaataaga gctaatgtat       420 ttttttttcta aaaaagttg aatgtggata caatatgatt atacattcat tagctatttt       480
aagtatattc tattttttt cccccaaaa gaacacaaat gtgttccgtc actttccatg        540
gagatcttag atctacgtgg tgcatttct aacactccac gttcgctgta cggcattatt       600
tctccagcca gaaagaccga gacagcgacg ctgttgggcg ggcccgcggc ctgctctctc       660
tgcttcccca tgagattcac gggcatcgct cctcgctcgt gcctacgcga ccgcgccgat       720
ccacgtgacg tggcgcagca atcgttctta ctaggcgctt gcacgtgtcg ttcgcatgcg       780
aagcgtccac actgccaacg acctccttaa atatccttgt gatattcgcc ttacgatctc       840
acacttcgca cgcaaaggcc agtcgcagat ttggggttgaa tttgctgcgt tttggcagat    900
tttgagcgag agatattagg gaag                                              924

<210> SEQ ID NO 8
<211> LENGTH: 924
<212> TYPE: DNA
<213> ORGANISM: Artificial Sequence
<220> FEATURE:
<223> OTHER INFORMATION: Reverse complement XvPSap1F

<400> SEQUENCE: 8
cttccctaat atctctcgct caaaatctgc caaaacgcag caaattcaac ccaaatctgc        60
```

```
gactggcctt tgcgtgcgaa gtgtgagatc gtaaggcgaa tatcacaagg atatttaagg    120
aggtcgttgg cagtgtggac gcttcgcatg cgaacgacac gtgcaagcgc ctagtaagaa    180
cgattgctgc gccacgtcac gtggatcggc gcggtcgcgt aggcacgagc gaggagcgat    240
gcccgtgaat ctcatgggga agcagagaga gcaggccgcg ggcccgccca acagcgtcgc    300
tgtctcggtc tttctggctg agaaataat gccgtacagc gaacgtggag tgttagaaaa      360
tgcaccacgt agatctaaga tctccatgga aagtgacgga acacatttgt gttcttttgg    420
ggggaaaaaa aatagaatat acttaaaata gctaatgaat gtataatcat attgtatcca    480
cattcaactt ttttagaaa aaaaatacat tagctcttat tctagtctta tttactcatt      540
tcagaaaaga acactcggga gaaaaatcaa agaatgcacg tgaactttct tactttcggt    600
atacacattg gtatacgttg gatatcttgg ggtaattctt tggatcatct taatattttg    660
gagaaagtct tgagctgcaa ccttttgttt cagatcgaat gctattgatc ctctcgtgtt    720
tcatgctttt ttttctggga gctgtacctg cacatggatg ccatgaagtc ctctttattt    780
taaataagta aaaactctga ccaagttctt tagtcaggtc tatgataaaa tgagtgaaag    840
accgaattag ggtgatgatc catgaatttc tccctattta cagacaatta tttacgtctc    900
tatattgcca gctacccaga cagt                                            924

<210> SEQ ID NO 9
<211> LENGTH: 2083
<212> TYPE: DNA
<213> ORGANISM: Xerophyta viscosa

<400> SEQUENCE: 9
actgtctggg tagctggcaa tatagagacg taaataattg tctgtaaata gggagaaatt     60
catggatcat caccctaatt cggtctttca ctcattttat catagacctg actaaagaac    120
ttggtcagag ttttttactta tttaaaataa agaggacttc atggcatcca tgtgcaggta    180
cagctcccag aaaaaaaagc atgaaacacg agaggatcaa tagcattcga tctgaaacaa    240
aaggttgcag ctcaagactt tctccaaaat attaagatga tccaaagaat taccccaaga    300
tatccaacgt ataccaatgt gtataccgaa agtaagaaag ttcacgtgca ttctttgatt    360
tttctcccga gtgttctttt ctgaaatgag taaataagac tagaataaga gctaatgtat    420 ttttttttcta aaaaagttg aatgtggata caatatgatt atacattcat tagctatttt     480
aagtatattc tatttttttt ccccccaaaa gaacacaaat gtgttccgtc actttccatg    540
gggcaaatta caacttaggc tttatctag ttggtatgat cttaatttta ttatacttta     600
aacaacttat cgctaataat tttgttttga tttatgcgcc aattgtaaat aaatcggata    660
aatttgaaca ttaatacttt tagtcaaagt ttcaaaaaag aaaaagataa ctatgacgtt    720
agagtttgga atccagtcaa atggaactta tttttttagtt catcagaatc aacttgatga    780
gattttttgt actagacaat catcttgaat gatagatagg ggacttacca atcagccccc    840
catattttga aactttcaac gcgccccca atattttct ctttcaacgc gcccttccat      900
cacttttttc ttttcatcgc ccctccctca acttttggt cggacggaaa tacccctaaa    960
ataatttcat catttccacc cccaaacat ttatttagaa gtatttttg aaaaaaattt     1020 taacatgaaa gttttagacc ttgatgagat ctacaacttt tatgttgaaa gttttttccaa  1080 aaaatacttt tagatagata ttttgaaact ccgaagtgtt aatgggtcga cccgctaact  1140
tgcagaaata gaaaaacatc aagatctaca attttatgt tgaaagttt ttaaaaaat      1200
```

```
atagatagat atttgattta taattttaat attgaaagtt ttttcaaaaa atacttctag    1260
atagatattt tgggactctg gaatgttaca agtataggaa tatttttgtc tgtaaaaaat    1320
taatttttca gacaaagggc tgatcagtaa ggaatctggt cggggagct gttcggcaat     1380 ataagttcag ataggagaac taatcggata ttttccctta atttaattcc gatttgatac    1440
tattaagaat gaaaacatcc taataattgt gaccacttta tagcaccaca tttattttaa    1500
ttttaaatct tttaaatctt agaattggac agggtgctta tgataacaaa cttgttccta    1560
tcaacaactg catgttagac agcgccgaat ttacagtcct actgggcgcc acttttcaac    1620
ccacatcatc aagatgaaca ccacgttatc ttcatccgct ccaaccacat ggtccagcgc    1680
cactggccaa gaccgccagc cagccaggcc atccaacgtg gtgcattttc taacactcca    1740
cgttcgctgt acggcattat ttctccagcc agaaagaccg agacagcgac gctgttgggc    1800
gggcccgcgg cctgctctct ctgcttcccc atgagattca cgggcatcgc tcctcgctcg    1860
tgcctacgcg accgcgccga tccacgtgac gtggcgcagc aatcgttctt actaggcgct    1920
tgcacgtgtc gttcgcatgc gaagcgtcca cactgccaac gacctcctta aatatccttg    1980
tgatattcgc cttacgatct cacacttcgc acgcaaaggc cagtcgcaga tttgggttga    2040
attgctgcgt ttgccagatt ttgagcgaga gatattaggg aag                     2083

<210> SEQ ID NO 10
<211> LENGTH: 1656
<212> TYPE: DNA
<213> ORGANISM: Artificial Sequence
<220> FEATURE:
<223> OTHER INFORMATION: Luciferase gene

<400> SEQUENCE: 10
atggtcaccg acgccaaaaa cataaagaaa ggcccggcgc cattctatcc gctggaagat      60
ggaaccgctg gagagcaact gcataaggct atgaagagat acgccctggt tcctggaaca    120
attgctttta cagatgcaca tatcgaggtg gacatcactt acgctgagta cttcgaaatg    180
tccgttcggt tggcagaagc tatgaaacga tatgggctga atacaaatca cagaatcgtc    240
gtatgcagtg aaaactctct tcaattcttt atgccggtgt tgggcgcgtt atttatcgga    300
gttgcagttg cgcccgcgaa cgacatttat aatgaacgtg aattgctcaa cagtatgggc    360
atttcgcagc ctaccgtggt gttcgtttcc aaaaaggggt tgcaaaaaat tttgaacgtg    420
caaaaaaagc tcccaatcat ccaaaaaatt attatcatgg attctaaaac ggattaccag    480
ggatttcagt cgatgtacac gttcgtcaca tctcatctac ctcccggttt taatgaatac    540
gattttgtgc cagagtcctt cgatagggac aagacaattg cactgatcat gaactcctct    600
ggatctactg gtctgcctaa aggtgtcgct ctgcctcata gaactgcctg cgtgagattc    660
tcgcatgcca gagatcctat ttttggcaat caaatcattc cggatactgc gattttaagt    720
gttgttccat tccatcacgg ttttggaatg tttactacac tcggatattt gatatgtgga    780
tttcgagtcg tcttaatgta tagatttgaa gaagagctgt ttctgaggag ccttcaggat    840
tacaagattc aaagtgcgct gctggtgcca acccctattct ccttcttcgc caaaagcact    900
ctgattgaca atacgattt atctaattta cacgaaattg cttctggtgg cgctcccctc    960
tctaaggaag tcggggaagc ggttgccaag aggttccatc tgccaggtat caggcaagga    1020
tatgggctca ctgagactac atcagctatt ctgattacac ccgagggggga tgataaaccg    1080 ggcgcggtcg gtaaagttgt tccattttt gaagcgaagg ttgtggatct ggataccggg    1140
aaaacgctgg gcgttaatca agagggcgaa ctgtgtgtga gaggtcctat gattatgtcc    1200
```

```
ggttatgtaa acaatccgga agcgaccaac gccttgattg acaaggatgg atggctacat    1260
tctggagaca tagcttactg ggacgaagac gaacacttct tcatcgttga ccgcctgaag    1320
tctctgatta agtacaaagg ctatcaggtg gctcccgctg aattggaatc catcttgctc    1380
caacacccca acatcttcga cgcaggtgtc gcaggtcttc ccgacgatga cgccggtgaa    1440
cttcccgccg ccgttgttgt tttggagcac ggaaagacga tgacggaaaa agagatcgtg    1500
gattacgtcg ccagtcaagt aacaaccgcg aaaaagttgc gcggaggagt tgtgtttgtg    1560
gacgaagtac cgaaaggtct taccggaaaa ctcgacgcaa gaaaaatcag agagatcctc    1620
ataaaggcca gaagggcgg aaagatcgcc gtgtaa                                1656
```

<210> SEQ ID NO 11
<211> LENGTH: 300
<212> TYPE: DNA
<213> ORGANISM: Unknown
<220> FEATURE:
<223> OTHER INFORMATION: Nos terminator

<400> SEQUENCE: 11

```
gagtacggtg ggtagcccga tcgttcaaac atttggcaat aaagtttctt aagattgaat     60
cctgttgccg gtcttgcgat gattatcata taatttctgt tgaattacgt taagcatgta    120
ataattaaca tgtaatgcat gacgttattt atgagatggg ttttatgat tagagtcccg     180 caattataca tttaatacgc gatagaaaac aaaatatagc gcgcaaacta ggataaatta    240
tcgcgcgcgg tgtcatctat gttactagat ccctaggcta tctgtcactt catcaaaagg    300
```

<210> SEQ ID NO 12
<211> LENGTH: 28
<212> TYPE: DNA
<213> ORGANISM: Artificial Sequence
<220> FEATURE:
<223> OTHER INFORMATION: Oligonucleotide: Primer A

<400> SEQUENCE: 12

```
cagatctacg tggtgcattt tctaacac                                         28
```

<210> SEQ ID NO 13
<211> LENGTH: 28
<212> TYPE: DNA
<213> ORGANISM: Artificial Sequence
<220> FEATURE:
<223> OTHER INFORMATION: Oligonucleotide: Primer B

<400> SEQUENCE: 13

```
cagatctatc ttagaattgg acagggtg                                         28
```

<210> SEQ ID NO 14
<211> LENGTH: 26
<212> TYPE: DNA
<213> ORGANISM: Artificial Sequence
<220> FEATURE:
<223> OTHER INFORMATION: Oligonucleotide: Primer C

<400> SEQUENCE: 14

```
aagatctcca tggaaagtga cggaac                                           26
```

<210> SEQ ID NO 15
<211> LENGTH: 28
<212> TYPE: DNA
<213> ORGANISM: Artificial Sequence
<220> FEATURE:

<223> OTHER INFORMATION: Oligonucleotide: Primer D

<400> SEQUENCE: 15
aagatctaat gcacgtgaac tttcttac                                          28

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide: EcoRI-XvPSap1-F

<400> SEQUENCE: 16
ggaattcact gtctggtagc tgg                                               23

<210> SEQ ID NO 17
<211> LENGTH: 28
<212> TYPE: DNA
<213> ORGANISM: Artificial Sequence
<220> FEATURE:
<223> OTHER INFORMATION: Oligonucleotide: BamHI-XvPSap1-R

<400> SEQUENCE: 17
tccggatcct ccctaatatc tctcgctc                                          28

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide: BarI

<400> SEQUENCE: 18
ggtctgcacc atcgtcaacc                                                   20

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide: BarII

<400> SEQUENCE: 19
gtcatgccag ttcccgtgct                                                   20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide: luc-R3

<400> SEQUENCE: 20
agcagcgcac tttgaatctt                                                   20

<210> SEQ ID NO 21
<211> LENGTH: 23
<212> TYPE: DNA
<213> ORGANISM: Artificial Sequence
<220> FEATURE:
<223> OTHER INFORMATION: Oligonucleotide: RT-luc-F2

<400> SEQUENCE: 21
atccagaagc caccaacgcc ttg                                               23

<210> SEQ ID NO 22
<211> LENGTH: 23
<212> TYPE: DNA
<213> ORGANISM: Artificial Sequence
<220> FEATURE:
<223> OTHER INFORMATION: Oligonucleotide: RT-luc-R2

<400> SEQUENCE: 22
cgaagatgtt ggcgtgttgg agc                                              23

<210> SEQ ID NO 23
<211> LENGTH: 24
<212> TYPE: DNA
<213> ORGANISM: Artificial Sequence
<220> FEATURE:
<223> OTHER INFORMATION: Oligonucleotide: RT-18S-F3

<400> SEQUENCE: 23
gcagcggaag tttgaggcaa taac                                             24

<210> SEQ ID NO 24
<211> LENGTH: 22
<212> TYPE: DNA
<213> ORGANISM: Artificial Sequence
<220> FEATURE:
<223> OTHER INFORMATION: Oligonucleotide: RT-18S-R3

<400> SEQUENCE: 24
cgacctgatg actcgcgctt ac                                               22

<210> SEQ ID NO 25
<211> LENGTH: 26
<212> TYPE: DNA
<213> ORGANISM: Artificial Sequence
<220> FEATURE:
<223> OTHER INFORMATION: Oligonucleotide: RT-Rib-F3

<400> SEQUENCE: 25
gcagattcag gacaacaaca cccttg                                           26

<210> SEQ ID NO 26
<211> LENGTH: 23
<212> TYPE: DNA
<213> ORGANISM: Artificial Sequence
<220> FEATURE:
<223> OTHER INFORMATION: Oligonucleotide: RT-Rib-R3

<400> SEQUENCE: 26
ttgttggcaa cgtccgaagc atc                                              23

<210> SEQ ID NO 27
<211> LENGTH: 22
<212> TYPE: DNA
<213> ORGANISM: Artificial Sequence
<220> FEATURE:
<223> OTHER INFORMATION: Oligonucleotide: RT-EF-F1

<400> SEQUENCE: 27
ggtcaccaag gctgctcaga ag                                               22

<210> SEQ ID NO 28
<211> LENGTH: 20
<212> TYPE: DNA
<213> ORGANISM: Artificial Sequence
<220> FEATURE:
<223> OTHER INFORMATION: Oligonucleotide: RT-EF-R1

<400> SEQUENCE: 28
gcctgtcaac cacccagctc                                                         20

<210> SEQ ID NO 29
<211> LENGTH: 9189
<212> TYPE: DNA
<213> ORGANISM: Artificial Sequence
<220> FEATURE:
<223> OTHER INFORMATION: pTF101.1 vector

<400> SEQUENCE: 29

| | | | | | |
|---|---|---|---|---|---|
| agtactttaa | agtactttaa | agtactttaa | agtactttga | tccaacccct | ccgctgctat | 60 |
| agtgcagtcg | gcttctgacg | ttcagtgcag | ccgtcttctg | aaaacgacat | gtcgcacaag | 120 |
| tcctaagtta | cgcgacaggc | tgccgccctg | ccctttcct | ggcgttttct | tgtcgcgtgt | 180 |
| tttagtcgca | taaagtagaa | tacttgcgac | tagaaccgga | gacattacgc | catgaacaag | 240 |
| agcgccgccg | ctggcctgct | gggctatgcc | cgcgtcagca | ccgacgacca | ggacttgacc | 300 |
| aaccaacggg | ccgaactgca | cgcggccggc | tgcaccaagc | tgttttccga | gaagatcacc | 360 |
| ggcaccaggc | gcgaccgccc | ggagctggcc | aggatgcttg | accacctacg | ccctggcgac | 420 |
| gttgtgacag | tgaccaggct | agaccgcctg | gcccgcagca | cccgcgacct | actggacatt | 480 |
| gccgagcgca | tccaggaggc | cggcgcgggc | ctgcgtagcc | tggcagagcc | gtgggccgac | 540 |
| accaccacgc | cggccggccg | catggtgttg | accgtgttcg | ccggcattgc | cgagttcgag | 600 |
| cgttccctaa | tcatcgaccg | cacccggagc | gggcgcgagg | ccgccaaggc | ccgaggcgtg | 660 |
| aagtttggcc | cccgccctac | cctcaccccg | gcacagatcg | cgcacgcccg | cgagctgatc | 720 |
| gaccaggaag | gccgcaccgt | gaaagaggcg | gctgcactgc | ttgcgtgca | tcgctcgacc | 780 |
| ctgtaccgcg | cacttgagcg | cagcgaggaa | gtgacgccca | ccgaggccag | gcggcgcggt | 840 |
| gccttccgtg | aggacgcatt | gaccgaggcc | gacgccctgg | cggccgccga | gaatgaacgc | 900 |
| caagaggaac | aagcatgaaa | ccgcaccagg | acggccagga | cgaaccgttt | ttcattaccg | 960 |
| aagagatcga | ggcggagatg | atcgcggccg | ggtacgtgtt | cgagccgccc | gcgcacgtct | 1020 |
| caaccgtgcg | gctgcatgaa | atcctggccg | gtttgtctga | tgccaagctg | gcggcctggc | 1080 |
| cggccagctt | ggccgctgaa | gaaaccgagc | gccgccgtct | aaaaggtgga | tgtgtatttg | 1140 |
| agtaaaacag | cttgcgtcat | gcggtcgctg | cgtatatgat | gcgatgagta | aataaacaaa | 1200 |
| tacgcaaggg | gaacgcatga | aggttatcgc | tgtacttaac | cagaaaggcg | ggtcaggcaa | 1260 |
| gacgaccatc | gcaacccatc | tagcccgcgc | cctgcaactc | gccggggccg | atgttctgtt | 1320 |
| agtcgattcc | gatccccagg | gcagtgcccg | cgattgggcg | gccgtgcggg | aagatcaacc | 1380 |
| gctaaccgtt | gtcggcatcg | accgcccgac | gattgaccgc | gacgtgaagg | ccatcggccg | 1440 |
| gcgcgacttc | gtagtgatcg | acggagcgcc | ccaggcggcg | gacttggctg | tgtccgcgat | 1500 |
| caaggcagcc | gacttcgtgc | tgattccggt | gcagccaagc | ccttacgaca | tatgggccac | 1560 |
| cgccgacctg | gtggagctgg | ttaagcagcg | cattgaggtc | acggatggaa | ggctacaagc | 1620 |
| ggcctttgtc | gtgtcgcggg | cgatcaaagg | cacgcgcatc | ggcggtgagg | ttgccgaggc | 1680 |
| gctgccgggg | tacgagctgc | ccattcttga | gtcccgtatc | acgcagcgcg | tgagctaccc | 1740 |
| aggcactgcc | gccgccggca | caaccgttct | tgaatcagaa | cccgagggcg | acgctgcccg | 1800 |
| cgaggtccag | gcgctggccg | ctgaaattaa | atcaaaactc | atttgagtta | atgaggtaaa | 1860 |
| gagaaaatga | gcaaaagcac | aaacacgcta | agtgccggcc | gtccgagcgc | acgcagcagc | 1920 |
| aaggctgcaa | cgttggccag | cctggcagac | acgccagcca | tgaagcgggt | caactttcag | 1980 |

```
ttgccggcgg aggatcacac caagctgaag atgtacgcgg tacgccaagg caagaccatt    2040
accgagctgc tatctgaata catcgcgcag ctaccagagt aaatgagcaa atgaataaat    2100
gagtagatga atttagcgg ctaaaggagg cggcatggaa aatcaagaac aaccaggcac     2160
cgacgccgtg aatgcccca tgtgtggagg aacgggcggt tggccaggcg taagcggctg     2220
ggttgtctgc cggccctgca atggcactgg aacccccaag cccgaggaat cggcgtgagc    2280
ggtcgcaaac catccggccc ggtacaaatc ggcgcgcgc tgggtgatga cctggtggag     2340
aagttgaagg ccgcgcaggc cgcccagcgg caacgcatcg aggcagaagc acgccccggt    2400
gaatcgtggc aagcggccgc tgatcgaatc cgcaaagaat cccggcaacc gccggcagcc    2460
ggtgcgccgt cgattaggaa gccgcccaag ggcgacgagc aaccagattt tttcgttccg    2520
atgctctatg acgtgggcac ccgcgatagt cgcagcatca tggacgtggc cgttttccgt    2580
ctgtcgaagc gtgaccgacg agctggcgag gtgatccgct acgagcttcc agacgggcac    2640
gtagaggttt ccgcagggcc ggccggcatg ccagtgtgt gggattacga cctggtactg     2700
atggcggttt cccatctaac cgaatccatg aaccgatacc gggaagggaa gggagacaag    2760
cccggccgcg tgttccgtcc acacgttgcg gacgtactca agttctgccg gcgagccgat    2820
ggcggaaagc agaaagacga cctggtagaa acctgcattc ggttaaacac cacgcacgtt    2880
gccatgcagc gtacgaagaa ggccaagaac ggccgcctgg tgacggtatc cgagggtgaa    2940
gccttgatta gccgctacaa gatcgtaaag agcgaaaccg ggcggccgga gtacatcgag    3000
atcgagctag ctgattggat gtaccgcgag atcacagaag gcaagaaccc ggacgtgctg    3060
acggttcacc ccgattactt tttgatcgat cccggcatcg gccgttttct ctaccgcctg    3120
gcacgccgcg ccgcaggcaa ggcagaagcc agatggttgt tcaagacgat ctacgaacgc    3180
agtggcagcg ccggagagtt caagaagttc tgtttcaccg tgcgcaagct gatcgggtca    3240
aatgacctgc cggagtacga tttgaaggag gaggcgggc aggctggccc gatcctagtc     3300
atgcgctacc gcaacctgat cgagggcgaa gcatccgccg gttcctaatg tacggagcag    3360
atgctagggc aaattgccct agcaggggaa aaaggtcgaa aaggtctctt tcctgtggat    3420
agcacgtaca ttgggaaccc aaagccgtac attgggaacc ggaacccgta cattgggaac    3480
ccaaagccgt acattgggaa ccggtcacac atgtaagtga ctgatataaa agagaaaaaa    3540
ggcgattttt ccgcctaaaa ctctttaaaa cttattaaaa ctcttaaaac ccgcctggcc    3600
tgtgcataac tgtctggcca gcgcacagcc gaagagctgc aaaaagcgcc tacccttcgg    3660
tcgctgcgct ccctacgccc cgccgcttcg cgtcggccta tcgcggccgc tggccgctca    3720
aaaatggctg gcctacggcc aggcaatcta ccagggcgcg gacaagccgc gccgtcgcca    3780
ctcgaccgcc ggcgcccaca tcaaggcacc ctgcctcgcg cgtttcggtg atgacggtga    3840
aaacctctga cacatgcagc tcccggagac ggtcacagct tgtctgtaag cggatgccgg    3900
gagcagacaa gcccgtcagg gcgcgtcagc gggtgttggc gggtgtcggg gcgcagccat    3960
gacccagtca cgtagcgata gcggagtgta tactggctta actatgcggc atcagagcag    4020
attgtactga gagtgcacca tatgcggtgt gaaataccgc acagatgcgt aaggagaaaa    4080
taccgcatca ggcgctcttc cgcttcctcg ctcactgact cgctgcgctc ggtcgttcgg    4140
ctgcggcgag cggtatcagc tcactcaaag gcggtaatac ggttatccac agaatcaggg    4200
gataacgcag gaaagaacat gtgagcaaaa ggccagcaaa aggccaggaa ccgtaaaaag    4260
gccgcgttgc tggcgttttt ccataggctc cgcccccctg acgagcatca caaaaatcga    4320
```

```
cgctcaagtc agaggtggcg aaacccgaca ggactataaa gataccaggc gtttccccct    4380
ggaagctccc tcgtgcgctc tcctgttccg accctgccgc ttaccggata cctgtccgcc    4440
tttctccctt cgggaagcgt ggcgctttct catagctcac gctgtaggta tctcagttcg    4500
gtgtaggtcg ttcgctccaa gctgggctgt gtgcacgaac ccccgttca gcccgaccgc     4560
tgcgccttat ccggtaacta tcgtcttgag tccaacccgg taagacacga cttatcgcca    4620
ctggcagcag ccactggtaa caggattagc agagcgaggt atgtaggcgg tgctacagag    4680
ttcttgaagt ggtggcctaa ctacggctac actagaagga cagtatttgg tatctgcgct    4740
ctgctgaagc cagttacctt cggaaaaaga gttggtagct cttgatccgg caaacaaacc    4800
accgctggta gcggtggttt ttttgtttgc aagcagcaga ttacgcgcag aaaaaaagga    4860
tctcaagaag atcctttgat cttttctacg ggtctgacg ctcagtggaa cgaaaactca     4920
cgttaaggga ttttggtcat gcatgatata tctcccaatt tgtgtagggc ttattatgca    4980
cgcttaaaaa taataaaagc agacttgacc tgatagtttg gctgtgagca attatgtgct    5040
tagtgcatct aacgcttgag ttaagccgcg ccgcgaagcg gcgtcggctt gaacgaattt    5100
ctagctagac attatttgcc gactaccttg gtgatctcgc ctttcacgta gtggacaaat    5160
tcttccaact gatctgcgcg cgaggccaag cgatcttctt cttgtccaag ataagcctgt    5220
ctagcttcaa gtatgacggg ctgatactgg gccggcaggc gctccattgc ccagtcggca    5280
gcgacatcct tcggcgcgat tttgccggtt actgcgctgt accaaatgcg ggacaacgta    5340
agcactacat ttcgctcatc gccagcccag tcgggcggcg agttccatag cgttaaggtt    5400
tcatttagcg cctcaaatag atcctgttca ggaaccggat caaagagttc ctccgccgct    5460
ggacctacca aggcaacgct atgttctctt gcttttgtca gcaagatagc cagatcaatg    5520
tcgatcgtgg ctggctcgaa gatacctgca agaatgtcat tgcgctgcca ttctccaaat    5580
tgcagttcgc gcttagctgg ataacgccac ggaatgatgt cgtcgtgcac aacaatggtg    5640
acttctacag cgcggagaat ctcgctctct ccaggggaag ccgaagtttc caaaaggtcg    5700
ttgatcaaag ctcgccgcgt tgtttcatca agccttacgg tcaccgtaac cagcaaatca    5760
atatcactgt gtggcttcag gccgccatcc actgcggagc cgtacaaatg tacgccagc     5820
aacgtcggtt cgagatggcg ctcgatgacg ccaactacct ctgatagttg agtcgatact    5880
tcggcgatca ccgcttcccc catgatgttt aactttgttt tagggcgact gccctgctgc    5940
gtaacatcgt tgctgctcca taacatcaaa catcgaccca cggcgtaacg cgcttgctgc    6000
ttggatgccc gaggcataga ctgtacccca aaaaaacagt cataacaagc catgaaaacc    6060
gccactgcgc cgttaccacc gctgcgttcg gtcaaggttc tggaccagtt gcgtgacggc    6120
agttacgcta cttgcattac agcttacgaa ccgaacgagg cttatgtcca ctgggttcgt    6180
gcccgaattg atcacaggca gcaacgctct gtcatcgtta caatcaacat gctaccctcc    6240
gcgagatcat ccgtgtttca aacccggcag cttagttgcc gttcttccga atagcatcgg    6300
taacatgagc aaagtctgcc gccttacaac ggctctcccg ctgacgccgt cccggactga    6360
tgggctgcct gtatcgagtg gtgattttgt gccgagctgc cggtcgggga gctgttggct    6420
ggctggtggc aggatatatt gtggtgtaaa caaattgacg cttagacaac ttaataacac    6480
attgcggacg ttttaatgt actgaattaa cgccgaattg ctctagcatt cgccattcag     6540
gctgcgcaac tgttgggaag ggcgatcggt gcgggcctct tcgctattac gccagctggc    6600
gaaaggggga tgtgctgcaa ggcgattaag ttgggtaacg ccagggtttt cccagtcacg    6660
acgttgtaaa acgacggcca gtgccaagct aattcgcttc aagacgtgct caaatcacta    6720
```

```
tttccacacc cctatatttc tattgcactc ccttttaact gttttttatt acaaaaatgc    6780
cctggaaaat gcactcccCt tttgtgtttg ttttttGtgt aaacgatgtt gtcaggtaat    6840
ttatttgtca gtctactatg gtggcccatt atattaatag caactgtcgg tccaatagac    6900
gacgtcgatt ttctgcattt gtttaaccac gtggatttta tgacatttta tattagttaa    6960
tttgtaaaac ctacccaatt aaagacctca tatgttctaa agactaatac ttaatgataa    7020
caattttctt ttagtgaaga aagggataat tagtaaatat ggaacaaggg cagaagattt    7080
attaaagccg cggtaagaga caacaagtag gtacgtggag tgtcttaggt gacttaccca    7140
cataacataa agtgacatta acaaacatag ctaatgctcc tatttgaata gtgcatatca    7200
gcataccTta tTacatatag ataggagcaa actctagcta gattgttgag cagatctcgg    7260
tgacgggcag gaccggacgg ggcggtaccg gcaggctgaa gtccagctgc cagaaaccca    7320
cgtcatgcca gttcccgtgc ttgaagccgg ccgcccgcag catgccgcgg ggggcatatc    7380
cgagcgcctc gtgcatgcgc acgctcgggt cgttgggcag cccgatgaca gcgaccacgc    7440
tcttgaagcc ctgtgcctcc agggacttca gcaggtgggt gtagagcgtg gagcccagtc    7500
ccgtccgctg gtggcgggcg gagacgtaca cggtcgactc ggccgtccag tcgtaggcgt    7560
tgcgtgcctt ccaggggccc gcgtaggcga tgccggcgac ctcgccgtcc acctcggcga    7620
cgagccaggg atagcgctcc cgcagacgga cgaggtcgtc cgtccactcc tgcggttcct    7680
gcggctcggt acggaagttg accgtgcttg tctcgatgta gtggttgacg atggtgcaga    7740
ccgccggcat gtccgcctcg gtggcacggc ggatgtcggc cgggcgtcgt tctgggctca    7800
tggtagatcc cccgttcgta aatggtgaaa attttcagaa aattgctttt gctttaaaag    7860
aaatgattta aattgctgca atagaagtag aatgcttgat tgcttgagat tcgtttgttt    7920
tgtatatgtt gtgttgagaa ttaattctcg aggtcctctc caaatgaaat gaacttcctt    7980
atatagagga agggtcttgc gaaggatagt gggattgtgc gtcatccctt acgtcagtgg    8040
agatatcaca tcaatccact tgctttgaag acgtggttgg aacgtcttct ttttccacga    8100
tgctcctcgt gggtgggggt ccatcttttg gaccactgtc ggtagaggca tcttgaacga    8160
tagccttTcc tttatcgcaa tgatggcatt tgtaggagcc accttccttt tccactatct    8220
tcacaataaa gtgacagata gctgggcaat ggaatccgag gaggtttccg gatattaccc    8280
tttgttgaaa agtctcaatt gcccttTggt cttctgagac tgtatctttg atattttTgg    8340
agtagacaag tgtgtcgtgc tccaccatgt tatcacatca atccacttgc tttgaagacg    8400
tggttggaac gtcttctttt tccacgatgc tcctcgtggg tggggtcca tctttgggac    8460 cactgtcggc agaggcatct tcaacgatgg ccttTccttt atcgcaatga tggcatttgt    8520
aggagccacc ttccttttcc actatcttca caataaagtg acagatagct gggcaatgga    8580
atccgaggag gtttccggat attcccttt gttgaaaagt ctcaattgcc ctttggtctt    8640
ctgagactgt atctttgata ttttTggagt agacaagtgt gtcgtgctcc accatgttga    8700
cctgcaggca tgcaagcttg catgcctgca ggtcgactct agaggatccc cgggtaccga    8760
gctcgaattc gtaatcatgt catagctgtt tcctgtgtga attgttatc cgctcacaat    8820 tccacacaac atacgagccg gaagcataaa gtgtaaagcc tggggtgcct aatgagtgag    8880
ctaactcaca ttaattgcgt tgcgctcact gcccgctttc cagtcgggaa acctgtcgtg    8940
ccagctgcat taatgaatcg gccaacgcgc ggggagaggc ggtttgcgta ttggagcttg    9000
agcttggatc agattgtcgt ttcccgcctt cagtttaaac tatcagtgtt tgacaggata    9060
```

```
tattggcggg taaacctaag agaaaagagc gtttattaga ataatcggat atttaaaagg    9120
gcgtgaaaag gtttatccgt tcgtccattt gtatgtgcat gccaaccaca gggttcccct    9180
cgggatcaa                                                            9189

<210> SEQ ID NO 30
<211> LENGTH: 1107
<212> TYPE: DNA
<213> ORGANISM: Artificial Sequence
<220> FEATURE:
<223> OTHER INFORMATION: Consensus sequence

<400> SEQUENCE: 30
actgtctggg tagctggcaa tatagagacg taaataattg tctgtaaata gggagaaatt      60
catggatcat caccctaatt cggtctttca ctcattttat catagacctg actaaagaac     120
ttggtcagag ttttttactta tttaaaataa agaggacttc atggcatcca tgtgcaggta    180
cagctcccag aaaaaaaagc atgaaacacg agaggatcaa tagcattcga tctgaaacaa    240
aaggttgcag ctcaagactt tctccaaaat attaagatga tccaaagaat taccccaaga    300
tatccaacgt ataccaatgt gtataccgaa agtaagaaag ttcacgtgca ttctttgatt    360
tttctcccga gtgttctttt ctgaaatgag taaataagac tagaataaga gctaatgtat    420
tttttttcta aaaaagttg aatgtggata caatatgatt atacattcat tagctatttt     480
aagtatattc tattttttt ccccccaaaa gaacacaaat gtgttccgtc actttccatg     540
tcttagaatt ggacagggtg cttatgatac aacttgttcc tatcaacaac tgcatgttag    600
acagcgccga atttacagtc ctactgggcg ccacttttca acccacatca tcaagatgaa    660
caccacgtta tcttcatccg ctccaaccac atggtccagc gccactggcc aagaccgcca    720
gccagccagg ccatccaacg tggtgcattt tctaacactc cacgttcgct gtacggcatt    780
atttctccag ccagaaagac cgagacagcg acgctgttgg gcgggcccgc ggcctgctct    840
ctctgcttcc ccatgagatt cacgggcatc gctcctcgct cgtgcctacg cgaccgcgcc    900
gatccacgtg acgtggcgca gcaatcgttc ttactaggcg cttgcacgtg tcgttcgcat    960
gcgaagcgtc cacactgcca acgacctcct taaatatcct tgtgatattc gccttacgat   1020
gcgaagcgtc cacactgcca acgacctcct taaatatcct tgtgatattc gccttacgat   1080
gattttgagc gagagatatt agggaag                                        1107

<210> SEQ ID NO 31
<211> LENGTH: 10
<212> TYPE: DNA
<213> ORGANISM: Artificial Sequence
<220> FEATURE:
<223> OTHER INFORMATION: TC-rich repeat

<400> SEQUENCE: 31
actttctcca                                                              10

<210> SEQ ID NO 32
<211> LENGTH: 10
<212> TYPE: DNA
<213> ORGANISM: Artificial Sequence
<220> FEATURE:
<223> OTHER INFORMATION: TC-rich repeat

<400> SEQUENCE: 32
attttctaac                                                              10
```

```
<210> SEQ ID NO 33
<211> LENGTH: 6
<212> TYPE: DNA
<213> ORGANISM: Artificial Sequence
<220> FEATURE:
<223> OTHER INFORMATION: MYB transcription factor binding site

<400> SEQUENCE: 33 caactg                                                                 6

<210> SEQ ID NO 34
<211> LENGTH: 6
<212> TYPE: DNA
<213> ORGANISM: Artificial Sequence
<220> FEATURE:
<223> OTHER INFORMATION: ABA-responsive element

<400> SEQUENCE: 34 cacgtg                                                                 6

<210> SEQ ID NO 35
<211> LENGTH: 7
<212> TYPE: DNA
<213> ORGANISM: Artificial Sequence
<220> FEATURE:
<223> OTHER INFORMATION: ABA-responsive element

<400> SEQUENCE: 35 acgtggc                                                                7

<210> SEQ ID NO 36
<211> LENGTH: 10
<212> TYPE: DNA
<213> ORGANISM: Artificial Sequence
<220> FEATURE:
<223> OTHER INFORMATION: ABA-responsive element

<400> SEQUENCE: 36
tgcacgtgtc                                                            10
```